US011781142B2

(12) United States Patent
Zajac-Kaye et al.

(10) Patent No.: US 11,781,142 B2
(45) Date of Patent: Oct. 10, 2023

(54) AAV DELIVERY OF SHRNA FOR TREATMENT OF PANCREATIC CANCER

(71) Applicant: University of Florida Research Foundation, Incorporated, Gainesville, FL (US)

(72) Inventors: Maria Zajac-Kaye, Gainesville, FL (US); Kyungah Maeng, Cambridge, MA (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 727 days.

(21) Appl. No.: 16/347,461

(22) PCT Filed: Nov. 3, 2017

(86) PCT No.: PCT/US2017/059843
§ 371 (c)(1),
(2) Date: May 3, 2019

(87) PCT Pub. No.: WO2018/132155
PCT Pub. Date: Jul. 19, 2018

(65) Prior Publication Data
US 2019/0256858 A1 Aug. 22, 2019

Related U.S. Application Data

(60) Provisional application No. 62/416,893, filed on Nov. 3, 2016.

(51) Int. Cl.
| | | |
|---|---|---|
| C12N 15/113 | (2010.01) |
| C12N 15/864 | (2006.01) |
| A61P 35/00 | (2006.01) |
| C12N 7/00 | (2006.01) |
| A01K 67/027 | (2006.01) |

(52) U.S. Cl.
CPC ...... *C12N 15/1137* (2013.01); *A01K 67/0278* (2013.01); *A61P 35/00* (2018.01); *C12N 7/00* (2013.01); *A01K 2217/072* (2013.01); *A01K 2217/075* (2013.01); *A01K 2227/105* (2013.01); *A01K 2267/0331* (2013.01); *C12N 2310/11* (2013.01); *C12N 2310/122* (2013.01); *C12N 2310/14* (2013.01); *C12N 2310/335* (2013.01); *C12N 2310/531* (2013.01); *C12N 2320/32* (2013.01); *C12N 2330/51* (2013.01); *C12N 2750/14142* (2013.01); *C12N 2750/14143* (2013.01)

(58) Field of Classification Search
CPC .............. C12N 15/113; C12N 2310/14; C12N 15/8645
See application file for complete search history.

(56) References Cited

U.S. PATENT DOCUMENTS

| | | |
|---|---|---|
| 2006/0089322 A1 | 4/2006 | Vincent et al. |
| 2007/0015238 A1 | 1/2007 | Snyder et al. |
| 2009/0258925 A1 | 10/2009 | Wahlestedt |
| 2012/0021994 A1* | 1/2012 | Sugiyama et al. ..... A61K 38/08 514/19.3 |
| 2013/0276169 A1 | 10/2013 | Poraty et al. |
| 2015/0203852 A1* | 7/2015 | Arora et al. ........ C12N 15/1137 |
| 2016/0151371 A1* | 6/2016 | Lee ...................... A61K 31/513 |

OTHER PUBLICATIONS

Flanagan et al. (2012) "Short Hairpin RNA Suppression of Thymidylate Synthase Produces DNA Mismatches and Results in Excellent Radiosensitization" International Journal of Radiation Oncology Biology Physics, 84(5), e613-e620. (Year: 2012).*
Maeng, Kyungah (May 2016) "Biological and Therapeutic Implications of Thymidylate Synthase in Pancreatic Neuroendocrine Tumors" (Publication No. 11007508) [Doctoral Dissertation, Graduate School of the University of Florida], 104 pages. (Year: 2016).*
Wang et al. (2006) "Widespread and Stable Pancreatic Gene Transfer by Adeno-Associated Virus Vectors via Different Routes" Diabetes, 55(4), 875-884. (Year: 2006).*
Kay et al. (2013) "Targeting Photoreceptors via Intravitreal Delivery Using Novel, Capsid-Mutated AAV Vectors" PloS one, 8(4), e62097, 12 pages. (Year: 2013).*
Kanungo, J. (Mar. 2017) "Puromycin-resistant lentiviral control shRNA vector, pLKO.1 induces unexpected cellular differentiation of P19 embryonic stem cells" Biochemical and Biophysical Research Communications 486, 481-485. (Year: 2017).*
Ge et al. (2010) "Minimal-length short hairpin RNAs: The relationship of structure and RNAi activity" RNA, 16:106-117. (Year: 2010).*
Mcintyre et al. (2011) "The effects of stem length and core placement on shRNA activity" BMC Molecular Biology, 12:34, 12 pages. (Year: 2011).*
Tai, Wanyi "Current Aspects of siRNA Bioconjugate for In Vitro and In Vivo Delivery" Molecules 2019, 24, 2211, 25 pages. (Year: 2019).*
Borel et al. (2014) "Recombinant AAV as a Platform for Translating the Therapeutic Potential of RNA Interference" Mol Ther. 22(4): 692-701. (Year: 2014).*
Gray et al. (2012) "Design and Construction of Functional AAV Vectors" In: Snyder, R., Moullier, P. (eds) Adeno-Associated Virus, Methods in Molecular Biology, vol. 807, pp. 25-46, Humana Press. (Year: 2012).*
International Search Report and Written Opinion dated Sep. 7, 2018 for Application No. PCT/US2017/059843.
International Preliminary Report on Patentability dated May 16, 2019 for Application No. PCT/US2017/059843.

* cited by examiner

*Primary Examiner* — James D Schultz
*Assistant Examiner* — James Joseph Graber
(74) *Attorney, Agent, or Firm* — Wolf, Greenfield & Sacks, P.C.

(57) ABSTRACT

Aspects of the disclosure relate to methods and compositions for treating pancreatic cancer (e.g., islet cell tumors). In some aspects, adeno-associated virus (AAV) may be used to deliver an interfering RNA that targets thymidylate synthase (TS).

15 Claims, 9 Drawing Sheets
Specification includes a Sequence Listing.

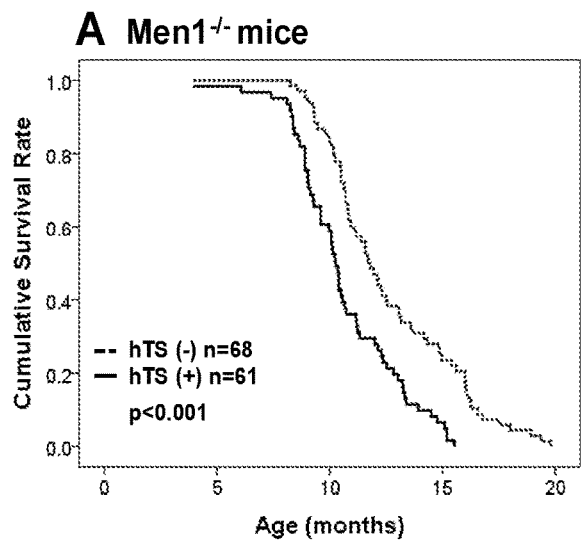
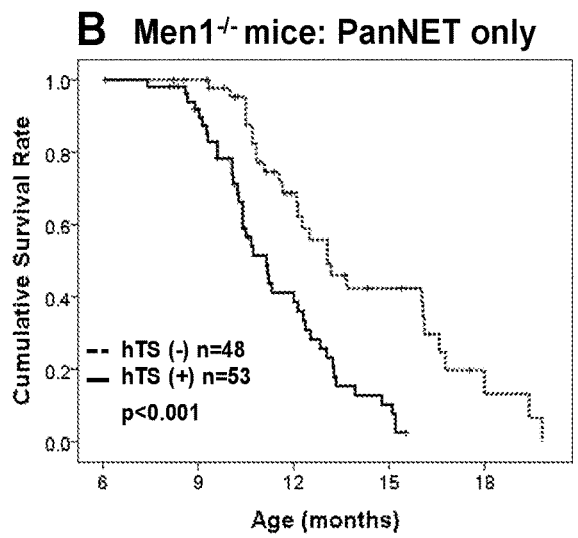
Figure 3A
Figure 3B
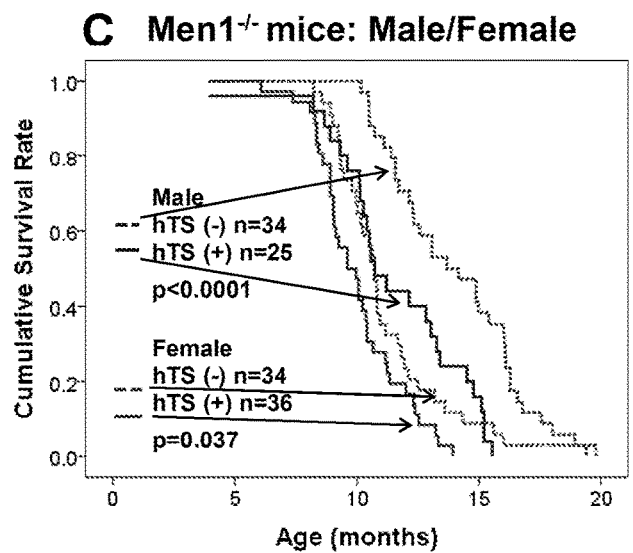
Figure 3C

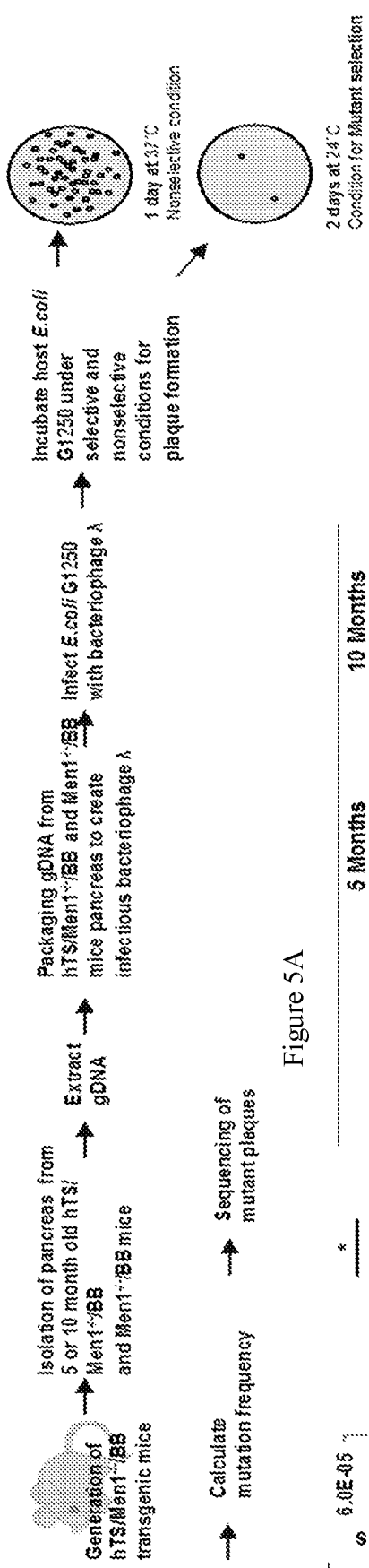
Figure 5A
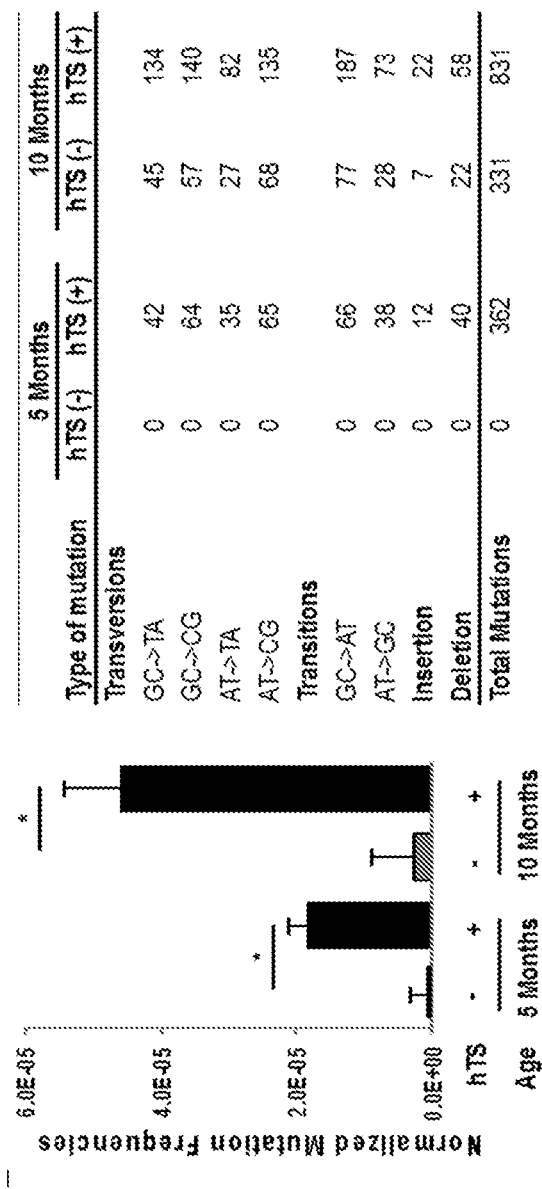
Figure 5B
| Type of mutation | 5 Months | | 10 Months | |
|---|---|---|---|---|
| | hTS (-) | hTS (+) | hTS (-) | hTS (+) |
| Transversions | | | | |
| GC→TA | 0 | 42 | 45 | 134 |
| GC→CG | 0 | 64 | 57 | 140 |
| AT→TA | 0 | 35 | 27 | 82 |
| AT→CG | 0 | 65 | 68 | 135 |
| Transitions | | | | |
| GC→AT | 0 | 66 | 77 | 187 |
| AT→GC | 0 | 38 | 28 | 73 |
| Insertion | 0 | 12 | 7 | 22 |
| Deletion | 0 | 40 | 22 | 58 |
| Total Mutations | 0 | 362 | 331 | 831 |
Figure 5C

AAV DELIVERY OF SHRNA FOR TREATMENT OF PANCREATIC CANCER

RELATED APPLICATIONS

This application is a national stage filing under 35 U.S.C § 371 of international application number PCT/US2017/059843, filed Nov. 3, 2017, which claims priority under 35 U.S.C. § 119(e) to U.S. provisional application No. 62/416,893, filed Nov. 3, 2016, entitled "AAV DELIVERY OF SHRNA FOR TREATMENT OF PANCREATIC CANCER," the content of each of which is incorporated herein by reference in its entirety.

BACKGROUND

The incidence of pancreatic neuroendocrine tumors (PanNET) is increasing and few therapeutic options are available. There remains a need for additional therapeutic treatments for PanNET and other pancreatic cancers.

SUMMARY

Aspects of the application relate to methods and compositions for treating pancreatic cancer (e.g., islet cell tumor).

Aspects of the disclosure also include a recombinant adeno-associated viral (rAAV) particle comprising a nucleic acid vector that comprises (a) a heterologous nucleic acid region comprising a sequence that encodes an interfering RNA that comprises a region of complementarity with a thymidylate synthase mRNA and (b) inverted terminal repeat (ITR) sequences flanking the heterologous nucleic acid region. In some embodiments, the interfering RNA is a small hairpin RNA (shRNA) or a microRNA. In some embodiments, the region of complementarity is 100% complementary to at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of any of SEQ ID NOs.: 6-11. In some embodiments, the interfering RNA comprises at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of SEQ ID NOs: 1, 2, 3 and/or 4, optionally where one or more Ts or Us in the sequence(s) may be substituted by one or more Us or Ts, respectively.

In some embodiments, the particle is an AAV8 particle or a modified AAV8 particle. In some embodiments, the modified AAV8 particle comprises an AAV8 capsid protein comprising a Y275F, Y447F, or Y733F mutation, or any combination thereof. In some embodiments, the AAV8 capsid protein comprises both a Y447F and Y733F mutation. In some embodiments, the interfering RNA is under expression control of a promoter sequence as described herein. In some embodiments, the interfering RNA is under expression control of an RNA polymerase III promoter. In some embodiments, the interfering RNA is under expression control of a pancreas-specific promoter, optionally wherein the pancreas-specific promoter is an islet-specific promoter, further optionally wherein the islet-specific promoter is an insulin promoter (e.g., a human insulin promoter).

In some embodiments, the disclosure includes a composition comprising any recombinant adeno-associated viral (rAAV) particle described herein, for example according to any one of the above-mentioned embodiments or another embodiment described herein. In some embodiments, the composition comprises one or more physiologically acceptable carriers and/or one or more physiologically acceptable adjuvants.

In some embodiments, the disclosure includes a method of decreasing thymidylate synthase expression in a cell (e.g., a human cell), the method comprising administering to the cell of an rAAV particle described herein or a composition described herein. In some embodiments, the cell is a cell of the pancreas.

In some embodiments, the disclosure includes a method of decreasing thymidylate synthase expression in a subject (e.g., a human subject), the method comprising administering to the subject an rAAV particle as described herein or a composition as described herein. In some embodiments, the administration results in delivery of the rAAV particle to the pancreas (e.g., to tumor cells in the pancreas, such as islet tumor cells). In some embodiments, the subject is a subject having one or more symptoms of a pancreatic condition, disease, or disorder (e.g., pancreatic cancer) or a subject that has been diagnosed with a pancreatic condition, disease, or disorder (e.g., pancreatic cancer).

In some embodiments, the disclosure includes a method of treating pancreatic cancer in a subject, the method comprising administering to the subject an rAAV particle as described herein or a composition as described herein. In some embodiments, the pancreatic cancer is islet cell carcinoma. In some embodiments, the subject is a human subject. In some embodiments, the subject is a subject having one or more symptoms of pancreatic cancer or a subject that has been diagnosed with pancreatic cancer.

In some embodiments, aspects of the application include a synthetic ribonucleic acid (RNA) molecule comprising a sense strand of sequence AACCUUUGGGAGAUGCACAUAUUUGUGAAGCCACAGAUGAAAUAUGUGCAUCUC CCAAAGUUUUUGUU (SEQ ID NO: 1) and an antisense strand of sequence AACAAAAACUUUGGGAGAUGCACAUAUUUCAUCUGUGGCUUCACAAAUAUGUGC AUCUCCCAAAGGUU (SEQ ID NO: 2). In some embodiments, the RNA is a small hairpin RNA (shRNA).

Other aspects include a shRNA having a targeted sequence that comprises RNA of sequence AAAUAUGUGCAUCUCCCAAAG (SEQ ID NO: 3) or RNA of sequence CUUUGGGAGAUGCACAUAUUU (SEQ ID NO: 4).

In some embodiments, the synthetic RNA further comprises an unpaired overhang sequence at the 5' and/or 3' end. In some embodiments, the unpaired overhang sequence comprises a sequence of repeating bases. In some embodiments, the sequence of repeating bases comprises repeating uracil (U) bases. In some embodiments, the unpaired overhang sequence is UU.

In some embodiments of any of the sequences herein, one or more Ts or Us in the sequence(s) may be substituted by one or more Us or Ts, respectively.

In some embodiments, a composition comprises a synthetic RNA described herein. In some embodiments, the composition further comprises one or more physiologically acceptable carriers and/or one or more physiologically acceptable adjuvants.

In some embodiments, the shRNA is encoded by a vector (e.g., a DNA vector). In some embodiments, the shRNA is selected from SEQ ID NOs: 1-4. In some embodiments, the vector is an expression plasmid. In some embodiments, the vector is a viral vector. In some embodiments, the viral vector is a recombinant adeno-associated viral (rAAV) vector. In some embodiments, a rAAV nucleic acid encodes an shRNA and is packaged in an rAAV particle.

In some embodiments, an rAAV particle or vector described herein may encode two or more shRNAs as described herein.

In some embodiments, a method of decreasing thymidylate synthase expression in a subject in provided. In some embodiments, the method comprises administering to the subject the composition or vector described herein. In some embodiments, the invention includes a method of treating pancreatic cancer in a subject, the method comprising administering to the subject a composition or a vector described herein. In some embodiments, the composition or vector is delivered using an rAAV. In some embodiments, the pancreatic cancer is islet cell carcinoma. In some embodiments, the rAAV is AAV8. In some embodiments, the interfering RNA is under expression control of promoter sequences. In some embodiments, the interfering RNA is shRNA, and wherein the shRNA is under expression control of an RNA polymerase III promoter. In some embodiments, the interfering RNA is shRNA, and wherein the shRNA is under expression control of a pancreas-specific promoter.

In some embodiments, the subject is a mammal. In some embodiments, the mammal is a rodent or a dog. In some embodiments, the mammal is a human.

These and other aspects are described in the following drawings, examples, and claims.

BRIEF DESCRIPTION OF DRAWINGS

The drawings and following brief descriptions provide non-limiting examples of aspects of the compositions and methods described herein.

(FIG. 2A) Schematic representation of breeding strategy. Arrows indicate primer location for genotyping analysis. (FIG. 2B) Genotyping results of hTS/Men1$^{-/-}$ and Men1$^{-/-}$ mice. (FIG. 2C) Immunoblot anlaysis for TS expression in the pancreases of hTS/Men1$^{-/-}$ and Men1$^{-/-}$ mice. (FIG. 2D) PanNET progression of hTS/Men1$^{-/-}$ GEMMs. Representative H&E images and pathological photographs of pancreatic islet lesions in hTS/fMen1-/- mice (Scale bar, 100 µm).

FIGS. 3A-3E show hTS overexpression significantly reduced survival of Men1-null mice. (FIG. 3A) Overall survival analysis of total Men1$^{-/-}$ vs. hTS/Men1$^{-/-}$ mice. (FIG. 3B) Survival analysis of Men1$^{-/-}$ vs. hTS/Men1$^{-/-}$ mice that developed only PanNETs. (FIG. 3C) mice. (FIG. 3D) Overall survival analysis of total Men1$^{+/-}$ vs. hTS/Men1$^{+/-}$ mice. (FIG. 3E) Separate survival analysis of male and female.

(FIG. 4A) Pancreatic islet lesions in Men1$^{-/-}$ vs. hTS/Men1$^{-/-}$ mice. Animals were euthanized at 5, 6.5 and 8 months and pancreas were isolated for histopathologic analysis (n=16 per group at each time point). (FIG. 4B) Pancreatic islet carcinoma incidence. The percentage of mice with islet tumor lesions is shown (*p<0.01, **p<0.001).

FIGS. 5A-5C show TS overexpression induces somatic mutations. (FIG. 5A) Overview of the λ Select-cII Mutation Detection System. (FIG. 5B) Mutation frequencies in Men1$^{-/-}$/BB and hTS/fMen1$^{-/-}$/BB mice (n=3 per group at each time point). (FIG. 5C) The type of mutations in the pancreas and tumors of Men1$^{-/-}$/BB and hTS/Men1$^{-/-}$/BB mice at 5 and 10 months of age.

(FIG. 6A) Immunofluorescence image of γH2AX foci in MEF-Men1$^{WT}$-vector, MEF-Men1$^{WT}$-hTS cells, MEF Men1$^{-/-}$-vector and MEF-Men1$^{-/-}$-hTS cells. Representative nuclei are shown (Scale bars, 10 µm). (FIG. 6B) Quantification of γH2AX foci (*p<0.01).

(FIG. 7A) Vector map of scAAV-mIP-GFP-NSshRNA construct. (FIG. 7B) Schematics of scAAV-mIP-GFP-NSshRNA (AAV-shNS) or scAAV-mIP-GFP-TSshRNA (AAV-shTS) treatment in hTS/Men1$^{-/-}$ mice. (FIG. 7C) Survival analysis of pancreas tissues from hTS/Men1 mice after TS shRNA injection (n=24 per group). (FIG. 7D) TS mRNA expression levels in tumors. (FIG. 7E) TS protein expression levels in tumors. (FIG. 7F) The percentage of islet tumor lesion (n=9 per group).

DETAILED DESCRIPTION

Figure 1:
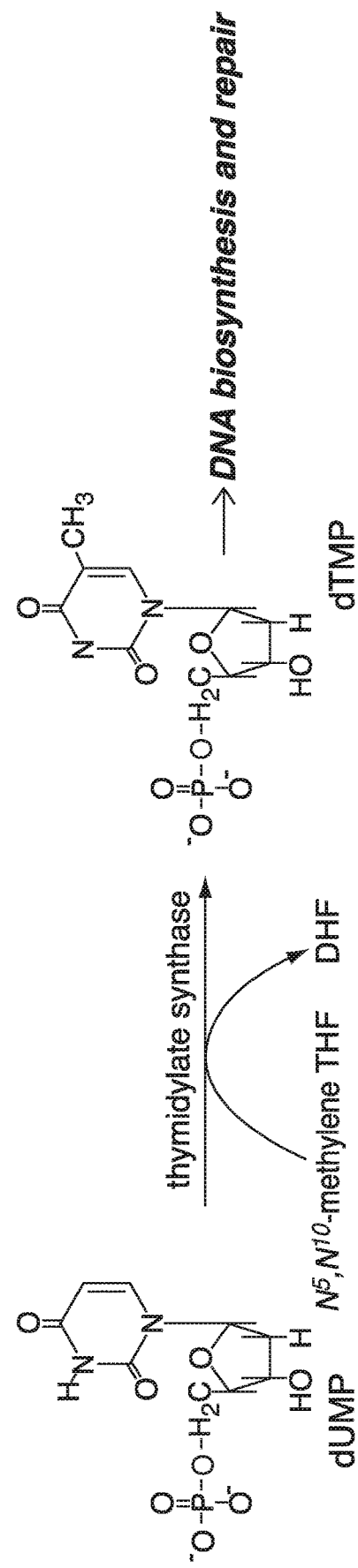
FIG. 1 shows the conversion of deoxyuridine monophosphate (dUMP) to deoxythymidine monophosphate (dTMP) with thymidylate synthetase.

Aspects of the application provide methods and compositions that are useful for treating pancreatic cancer (e.g., islet cell tumors). In some embodiments, a method of treating pancreatic cancer (e.g., PanNET) in a subject includes administering to the subject a composition or vector described herein. In some embodiments, the composition or vector for treating pancreatic cancer is a TS inhibitor. In some embodiments, the TS inhibitor is a TS shRNA (e.g., SEQ ID NOs: 1-4). In some embodiments, the TS shRNA can decrease cancer progression and increase survival of the subject.

The pancreas secretes enzymes that help digestion and hormones that assist with the regulation of the metabolism of sugars. The exocrine cells and endocrine cells of the pancreas can form different types of tumors in a subject. Pancreatic cancers can include exocrine pancreatic cancers (e.g., pancreatic adenocarcinoma) and pancreatic neuroendocrine tumors (e.g., PanNETs) or islet cell tumors (e.g., insulinomas). Pancreatic NETs may be functional or non-functional. Functional tumors make extra amounts of hormones, such as gastrin, insulin, and glucagon, that cause disease symptoms. Nonfunctional tumors do not make extra amounts of hormones. Signs and symptoms are caused by the tumor as it spreads and grows. Most nonfunctional tumors are malignant. Multiple endocrine neoplasia type 1 (MEN1) syndrome is a risk factor for PanNETs.

PanNETs can be detected or diagnosed via lab tests and/or imaging tests. Physical exam, blood chemistry studies, chromogranin A tests, CAT scans, MRI, somatostatin receptor scintigraphy, endoscopic ultrasound, endoscopic retrograde cholangiopancreatography (ERCP), angiogram, laparotomy, intraoperative ultrasound, biopsy, bone scans, specific PanNET lab tests, and combinations of these methods can be used for detection/diagnosis.

Thymidylate synthetase (EC 2.1.1.45) catalyzes the conversion of deoxyuridine monophosphate (dUMP) to deoxythymidine monophosphate (dTMP). Thymidine is one of the nucleotides in DNA. With inhibition of TS, an imbalance of deoxynucleotides and increased levels of dUTP arise. TS plays a crucial role in the early stages of DNA biosynthesis; DNA damage or deletion occur on a daily basis as a result of both endogenous and environmental factors. Therefore, synthesis and insertion of undamaged DNA is vital for normal body functions and avoidance of cancerous activity. In addition, inhibition in synthesis of important nucleotides necessary for cell growth is important. TS has become an important target for cancer treatment.

Human thymidylate synthetase (TS) is encoded by the gene TYMS (GenBank Ref. No. AAH83512). Non-limiting examples of cDNA sequences (SEQ ID NOs: 6-11) of TS are provided below, with the corresponding mRNA sequences having the Ts substituted with Us.

*Homo sapiens* thymidylate synthetase, mRNA (cDNA clone MGC:1590; GenBank Ref. No. BC002567);

SEQ ID NO: 6

```
   1   cgcgccactt ggcctgcctc cgtcccgccg cgccacttcg cctgcctccg tcccccgccc
  61   gccgcgccat gcctgtggcc ggctcggagc tgccgcgccg gcccttgccc ccgccgcac
 121   aggagcggga cgccgagccg cgtccgccgc acggggagct gcagtacctg gggcagatcc
 181   aacacatcct ccgctgcggc gtcaggaagg acgaccgcac gggcaccggc accctgtcgg
 241   tattcggcat gcaggcgcgc tacagcctga gagatgaatt ccctctgctg acaaccaaac
 301   gtgtgttctg aagggtgtt ttggaggagt tgctgtggtt atcaaggga tccacaaatg
 361   ctaaagagct gtcttccaag ggagtgaaaa tctgggatgc caatggatcc cgagactttt
 421   tggacagcct gggattctcc accagagaag aagggggactt gggcccagtt tatggcttcc
 481   agtggaggca ttttggggca gaatacagag atatggaatc agattattca ggacagggag
 541   ttgaccaact gcaaagagtg attgacacca tcaaaaccaa ccctgacgac agaagaatca
 601   tcatgtgcgc ttggaatcca agagatcttc ctctgatggc gctgcctcca tgccatgccc
 661   tctgccagtt ctatgtggtg aacagtgagc tgtcctgcca gctgtaccag agatcgggag
 721   acatgggcct cggtgtgcct ttcaacatcg ccagctacgc cctgctcacg tacatgattg
 781   cgcacatcac gggcctgaag ccaggtgact ttatacacac tttgggagat gcacatattt
 841   acctgaatca catcgagcca ctgaaaattc agcttcagcg agaacccaga cctttcccaa
 901   agctcaggat tcttcgaaaa gttgagaaaa ttgatgactt caaagctgaa gactttcaga
 961   ttgaaggta caatccgcat ccaactatta aaatggaaat ggctgtttag ggtgctttca
1021   aaggagcttg aaggatattg tcagtcttta ggggttgggc tggatgccga ggtaaaagtt
1081   cttttgctc taaaagaaga aggaactagg tcaaaaatct gtccgtgacc tatcagttat
1141   taatttttaa ggatgttgcc actggcaaat gtaactgtgc cagttctttc cataataaaa
1201   ggctttgagt taactcactg agggtatctg acaatgctga ggttatgaac aaagtgagga
1261   gaatgaaatg tatgtgctct tagcaaaaac atgtatgtgc atttcaatcc cacgtactta
1321   taaagaaggt tggtgaattt cacaagctat ttttggaata tttttagaat attttaagaa
1381   tttcacaagc tattccctca aatctgaggg agctgagtaa caccatcgat catgatgtag
1441   agtgtggtta tgaactttat agttgtttta tatgttgcta taataaagaa gtgttctgca
1501   ttcgtaaaaa aaaaaaaaaa aaaa
```

*Homo sapiens* thymidylate synthetase, mRNA (cDNA clone MGC:22884 IMAGE:4048625), complete cds (Genbank Ref. No. BC013919.1, SEQ ID NO: 7)

```
   1   ggggcgcgc ggaagggggtc ctgccaccgc gccacttggc ctgcctccgt cccgccgcgc
  61   cacttcgcct gcctccgtcc cccgccgcc gcgccatgcc tgtggccggc tcggagctgc
 121   cgcgccggcc cttgcccccc gccgcacagg agcgggacgc cgagccgcgt ccgccgcacg
 181   gggagctgca gtacctgggg cagatccaac acatcctccg ctgcggcgtc aggaaggacg
 241   accgcacggg caccggcacc ctgtcggtat tcggcatgca ggcgcgctac agcctgagag
 301   atgaattccc tctgctgaca accaaacgtg tgttctggaa gggtgttttg gaggagttgc
 361   tgtggtttat caagggatcc acaaatgcta aagagctgtc ttccaaggga gtgaaaatct
 421   gggatgccaa tggatcccga ctttttgg acagcctggg attctccacc agagaagaag
 481   gggacttggg cccagtttat ggcttccagt ggaggcattt tggggcagaa tacagagata
 541   tggaatcaga ttattcagga cagggagttg accaactgca aagagtgatt gacaccatca
 601   aaaccaaccc tgacgacaga gaatcatca tgtgcgcttg gaatccaaga gatcttcctc
 661   tgatggcgct gcctccatgc catgccctct gccagttcta tgtggtgaac agtgagctgt
```

-continued

```
 721   cctgccagct gtaccagaga tcgggagaca tgggcctcgg tgtgcctttc aacatcgcca
 781   gctacgccct gctcacgtac atgattgcgc acatcacggg cctgaagcca ggtgacttta
 841   tacacacttt gggagatgca catatttacc tgaatcacat cgagccactg aaaattcagc
 901   ttcagcgaga acccagacct ttcccaaagc tcaggattct tcgaaaagtt gagaaaattg
 961   atgacttcaa agctgaagac tttcagattg aagggtacaa tccgcatcca actattaaaa
1021   tggaaatggc tgtttagggt gctttcaaag gagctcgaag gatattgtca gtctttaggg
1081   gttgggctgg atgccgaggt aaaagttctt tttgctctaa agaaaaagg aactaggtca
1141   aaaatctgtc cgtgacctat cagttattaa ttttttaagga tgttgccact ggcaaatgta
1201   actgtgccag ttctttccat aataaaaggc tttgagttaa ctcactgagg gtatctgaca
1261   atgctgaggt tatgaacaaa gtgaggagaa tgaaatgtat gtgctcttag caaaaacatg
1321   tatgtgcatt tcaatcccac gtacttataa agaaggttgg tgaatttcac aagctatttt
1381   tggaatattt ttagaatatt ttaagaattt cacaagctat tccctcaaat ctgagggagc
1441   tgagtaacac catcgatcat gatgtagagt gtggttatga actttaaagt tatagttgtt
1501   ttatatgttg ctataataaa gaagtgttct gcattcgcca aaaaaaaaa aaaaaaaaa
1561   aaaaaaaaa
```

Synthetic construct Homo sapiens clone FLH058707.01L thymidylate synthetase (TYMS) mRNA, partial cds (Genbank Ref. No. AY893706.1, SEQ ID NO: 8)

```
   1   atgcctgtgg ccggctcgga gctgccgcgc cggcccttgc ccccgccgc acaggagcgg
  61   gacgccgagc cgcgtccgcc gcacggggag ctgcagtacc tgggcagat ccaacacatc
 121   ctccgctgcg gcgtcaggaa ggacgaccgc acgggcaccg gcaccctgtc ggtattcggc
 181   atgcaggcgc gctacagcct gagagatgaa ttccctctgc tgacaaccaa acgtgtgttc
 241   tggaagggtg ttttggagga gttgctgtgg tttatcaagg atccacaaa tgctaaagag
 301   ctgtcttcca agggagtgaa aatctgggat gccaatggat cccgagactt tttggacagc
 361   ctgggattct ccaccagaga agaaggggac ttgggcccag tttatggctt ccagtggagg
 421   cattttgggg cagaatacag agatatggaa tcagattatt caggacaggg agttgaccaa
 481   ctgcaaagag tgattgacac catcaaaacc aaccctgacg acagaagaat catcatgtgc
 541   gcttggaatc caagagatct tcctctgatg gcgctgcctc catgccatgc cctctgccag
 601   ttctatgtgg tgaacagtga gctgtcctgc cagctgtacc agagatcggg agacatgggc
 661   ctcggtgtgc ctttcaacat cgccagctac gccctgctca cgtacatgat tgcgcacatc
 721   acgggcctga agccaggtga ctttatacac actttgggag atgcacatat ttacctgaat
 781   cacatcgagc cactgaaaat tcagcttcag cgagaaccca gacctttccc aaagctcagg
 841   attcttcgaa agttgagaaa attgatgac ttcaaagctg aagactttca gattgaaggg
 901   tacaatccgc atccaactat taaaatggaa atggctgttt tg
```

Synthetic construct Homo sapiens clone FLH058712.01X thymidylate synthetase (TYMS) mRNA, complete cds (Genbank Ref. No. AY890751.1, SEQ ID NO: 9)

```
   1   atgcctgtgg ccggctcgga gctgccgcgc cggcccttgc ccccgccgc acaggagcgg
  61   gacgccgagc cgcgtccgcc gcacggggag ctgcagtacc tgggcagat ccaacacatc
 121   ctccgctgcg gcgtcaggaa ggacgaccgc acgggcaccg gcaccctgtc ggtattcggc
 181   atgcaggcgc gctacagcct gagagatgaa ttccctctgc tgacaaccaa acgtgtgttc
 241   tggaagggtg ttttggagga gttgctgtgg tttatcaagg atccacaaa tgctaaagag
 301   ctgtcttcca agggagtgaa aatctgggat gccaatggat cccgagactt tttggacagc
 361   ctgggattct ccaccagaga agaaggggac ttgggcccag tttatggctt ccagtggagg
 421   cattttgggg cagaatacag agatatggaa tcagattatt caggacaggg agttgaccaa
```

-continued

```
481   ctgcaaagag tgattgacac catcaaaacc aaccctgacg acagaagaat catcatgtgc 541   gcttggaatc caagagatct tcctctgatg gcgctgcctc catgccatgc cctctgccag 601   ttctatgtgg tgaacagtga gctgtcctgc cagctgtacc agagatcggg agacatgggc 661   ctcggtgtgc ctttcaacat cgccagctac gccctgctca cgtacatgat tgcgcacatc 721   acgggcctga agccaggtga ctttatacac actttgggag atgcacatat ttacctgaat 781   cacatcgagc cactgaaaat tcagcttcag cgagaaccca gacctttccc aaagctcagg 841   attcttcgaa aagttgagaa aattgatgac ttcaaagctg aagactttca gattgaaggg 901   tacaatccgc atccaactat taaaatggaa atggctgttt ag
```

Synthetic construct *Homo sapiens* clone FLH117831.01L thymidylate synthetase
(TYMS) mRNA, partial cds (Genbank Ref. No. AY890751.1, SEQ ID NO: 10)

```
  1   atgcctgtgg ccggctcgga gctgccgcgc cggcccttgc ccccgccgc acaggagcgg 61   gacgccgagc gcgtccgcc gcacggggag ctgcagtacc tgggcagat ccaacacatc 121   ctccgctgcg gcgtcaggaa ggacgaccgc acgggcaccg gcaccctgtc ggtattcggc 181   atgcaggcgc gctacagcct gagagatgaa ttccctctgc tgacaaccaa acgtgtgttc 241   tggaagggtg ttttggagga gttgctgtgg tttatcaagg atccacaaa tgctaaagag 301   ctgtcttcca agggagtgaa aatctgggat gccaatggat cccgagactt tttggacagc 361   ctgggattct ccaccagaga agaaggggac ttgggcccag tttatggctt ccagtggagg 421   cattttgggg cagaatacag agatatggaa tcagattatt caggacaggg agttgaccaa 481   ctgcaaagag tgattgacac catcaaaacc aaccctgacg acagaagaat catcatgtgc 541   gcttggaatc caagagatct tcctctgatg gcgctgcctc catgccatgc cctctgccag 601   ttctatgtgg tgaacagtga gctgtcctgc cagctgtacc agagatcggg agacatgggc 661   ctcggtgtgc ctttcaacat cgccagctac gccctgctca cgtacatgat tgcgcacatc 721   acgggcctga agccaggtga ctttatacac actttgggag atgcacatat ttacctgaat 781   cacatcgagc cactgaaaat tcagcttcag cgagaaccca gacctttccc aaagctcagg 841   attcttcgaa aagttgagaa aattgatgac ttcaaagctg aagactttca gattgaaggg 901   tacaatccgc atccaactat taaaatggaa atggctgttt tg
```

Synthetic construct *Homo sapiens* clone FLH117835.01X thymidylate synthetase
(TYMS) mRNA, complete cds (Genbank Ref. No. AY888178.1, SEQ ID NO: 11)

```
  1   atgcctgtgg ccggctcgga gctgccgcgc cggcccttgc ccccgccgc acaggagcgg 61   gacgccgagc gcgtccgcc gcacggggag ctgcagtacc tgggcagat ccaacacatc 121   ctccgctgcg gcgtcaggaa ggacgaccgc acgggcaccg gcaccctgtc ggtattcggc 181   atgcaggcgc gctacagcct gagagatgaa ttccctctgc tgacaaccaa acgtgtgttc 241   tggaagggtg ttttggagga gttgctgtgg tttatcaagg atccacaaa tgctaaagag 301   ctgtcttcca agggagtgaa aatctgggat gccaatggat cccgagactt tttggacagc 361   ctgggattct ccaccagaga agaaggggac ttgggcccag tttatggctt ccagtggagg 421   cattttgggg cagaatacag agatatggaa tcagattatt caggacaggg agttgaccaa 481   ctgcaaagag tgattgacac catcaaaacc aaccctgacg acagaagaat catcatgtgc 541   gcttggaatc caagagatct tcctctgatg gcgctgcctc catgccatgc cctctgccag 601   ttctatgtgg tgaacagtga gctgtcctgc cagctgtacc agagatcggg agacatgggc 661   ctcggtgtgc ctttcaacat cgccagctac gccctgctca cgtacatgat tgcgcacatc 721   acgggcctga agccaggtga ctttatacac actttgggag atgcacatat ttacctgaat 781   cacatcgagc cactgaaaat tcagcttcag cgagaaccca gacctttccc aaagctcagg
```

```
841    attcttcgaa aagttgagaa aattgatgac ttcaaagctg aagactttca gattgaaggg 901    tacaatccgc atccaactat taaaatggaa atggctgttt ag
```

In some aspects, the disclosure provides interfering RNAs (e.g., shRNAs or microRNAs) that contain a region of complementarity with a region of a TS mRNA (e.g., one of SEQ ID Nos: 6-11). Interfering RNAs, such as shRNAs or microRNAs, are further described herein. An interfering RNA may comprise a region of complementarity that is at least 80% complementary to (optionally one of at least 85%, 90%, 91%, 92%, 93%, 94%, 95%, 96%, 97%, 98%, 99% or 100% complementary to) the consecutive nucleotides of a TS mRNA (e.g., one of SEQ ID Nos: 6-11). In some embodiments, the region of complementarity is at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides long. In some embodiments, the region of the TS transcript is at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides long. In some embodiments, the interfering RNA is expressed by a nucleic acid as described herein (e.g. contained with an rAAV particle or vector). Methods for producing interfering RNAs are known in the art (see, e.g., Rao et al. Tissue-specific and cell type-specific RNA interference in vivo, Nature Protocols 1, 1494-1501 (2006); Moore et al. Short Hairpin RNA (shRNA): Design, Delivery, and Assessment of Gene Knockdown. Methods Mol Biol. 2010; 629: 141-158 and Wahid t al. MicroRNAs: Synthesis, mechanism, function, and recent clinical trials. Biochimica et Biophysica Acta. Volume 1803, Issue 11, November 2010, Pages 1231-1243) and are commercially available (see, e.g., services available from Dharmacon, Sigma-Aldrich, Origene, Thermofisher, System Biosciences, etc.).

In some embodiments, the interfering RNA is an shRNA. In some embodiments, an shRNA comprises an antisense sequence that is complementary to a target RNA and a sense sequence that is the reverse complement of the antisense sequence, typically separated by a spacer or loop sequence. A spacer or loop can be of a sufficient length to permit the antisense and sense sequences to anneal and form a double-stranded structure (or stem). The spacer can then be cleaved away to form a double-stranded RNA (and, optionally, subsequent processing steps that may result in addition or removal of one, two, three, four, or more nucleotides from the 3' end and/or the 5' end of either or both strands). In some embodiments, the stem of the shRNA comprises 19-29 basepairs and the loop comprises 4-8 nucleotides, optionally with a dinucleotide overhang at the 3' end of the shRNA. In some embodiments, the stem of the shRNA comprises a region of complementarity with a region of at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of a TS transcript (e.g., one of SEQ ID Nos: 6-11) as described herein and/or comprises at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of SEQ ID NOs: 1, 2, 3 and/or 4.

In some embodiments, the interfering RNA is a microRNA (miRNA). MiRNAs are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer. As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides, although miRNAs of up to 2000 nucleotides can be utilized. In some embodiments, the miRNA comprises a region of complementarity with a region of at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of a TS transcript (e.g., one of SEQ ID Nos: 6-11) as described herein and/or comprises at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of SEQ ID NOs: 1, 2, 3 and/or 4.

In some embodiments, the interfering RNA is under expression control of a promoter sequence as described herein. In some embodiments, the interfering RNA is under expression control of an RNA polymerase III promoter. In some embodiments, the interfering RNA is under expression control of a pancreas-specific promoter, optionally wherein the pancreas-specific promoter is an islet-specific promoter, further optionally wherein the islet-specific promoter is an insulin promoter (e.g., a human insulin promoter). Promoters are described in more detail herein.

Aspects of the disclosure also include a recombinant adeno-associated viral (rAAV) particle comprising a nucleic acid vector that comprises (a) a heterologous nucleic acid region comprising a sequence that encodes an interfering RNA that comprises a region of complementarity with a thymidylate synthase mRNA and (b) inverted terminal repeat (ITR) sequences flanking the heterologous nucleic acid region. In some embodiments, the interfering RNA is a small hairpin RNA (shRNA) or a microRNA. In some embodiments, the region of complementarity is complementary to at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of any of SEQ ID NOs.: 6-11. In some embodiments, the interfering RNA comprises at least 8 (e.g., at least 8, at least 9, at least 10, at least 11, at least 12, at least 13, at least 14, at least 15, at least 16, at least 17, at least 18, at least 19, at least 20, or at least 21, e.g., 8, 9, 10, 11, 12, 13, 14, 15, 16, 17, 18, 19, 20, or 21) contiguous nucleotides of SEQ ID NOs: 1, 2, 3 and/or 4.

In some embodiments, the particle is an AAV8 particle or a modified AAV8 particle. AAV8 particles and capsid proteins (including modified capsid proteins) are further described herein. In some embodiments, the modified AAV8 particle comprises an AAV8 capsid protein comprising at least one phenylalanine-to-tyrosine mutation, e.g., a Y275F, Y447F, or Y733F mutation, or any combination thereof (amino acid positions relative to the AAV8 VP1 protein, SEQ ID NO: 5). In some embodiments, the AAV8 capsid protein comprises both a Y447F and Y733F mutation (amino acid positions relative to the AAV8 VP1 protein, SEQ ID NO: 5). In some embodiments, the disclosure includes a method of decreasing thymidylate synthase expression in a cell, the method comprising administering to the cell of an rAAV particle described herein or a composition described herein. In some embodiments, the cell is a cell of the pancreas (e.g., a human pancreas cell).

In some embodiments, the disclosure includes a method of decreasing thymidylate synthase expression in a subject (e.g., a human subject), the method comprising administering to the subject an rAAV particle described herein or a composition described herein. In some embodiments, the administration results in delivery of the rAAV particle to the pancreas.

In some embodiments, the disclosure includes a method of treating pancreatic cancer in a subject, the method comprising administering to the subject an rAAV particle described herein or a composition described herein. In some embodiments, the pancreatic cancer is islet cell carcinoma. In some embodiments, the pancreatic cancer is a pancreatic cancer associated with an increase in TS expression compared to a baseline level of TS expression (e.g., in pancreatic cells that are not cancerous). In some embodiments, the subject is a human subject.

In some aspects, this application describes a synthetic ribonucleic acid (RNA) molecule comprising a sense strand of sequence AACCUUUGGGAGAUGCACAUAUUU-GUGAAGCCACAGAUGAAAUAUGUGCAUCUC CCAAAGUUUUUGUU (SEQ ID NO: 1) and an antisense strand of sequence AACAAAAACUUUGGGAGAUGCA-CAUAUUUCAUCUGUGGCUUCACAAAUAUGUGC AUCUCCCAAAGGUU (SEQ ID NO: 2).

In some embodiments, the RNA is a small interfering RNA (siRNA). In some embodiments, the RNA is a small hairpin RNA (shRNA). In some embodiments, the shRNA has a targeted sequence that comprises RNA of sequence AAAUAUGUGCAUCUCCCAAAG (SEQ ID NO: 3) or RNA of sequence CUUUGGGAGAUGCACAUAUUU (SEQ ID NO: 4). In some embodiments, the RNA is an artificial micro RNA (miRNA). In some embodiments, the synthetic RNA comprises an unpaired overhang sequence at the 5' and/or 3' end. In some embodiments, the unpaired overhang sequence comprises a sequence of repeating bases. In some embodiments, the sequence of repeating bases comprises repeating uracil (U) bases. In some embodiments, the unpaired overhang sequence is UU.

In some embodiments, a composition comprises any synthetic RNA variation described herein. In some embodiments, the composition further comprises one or more physiologically acceptable carriers and/or one or more physiologically acceptable adjuvants.

In some embodiments, the invention includes a vector encoding a shRNA described herein (e.g., SEQ ID NOs: 1-4). In some embodiments, the vector is an expression plasmid. In some embodiments, the vector is a viral vector.

In some embodiments, the viral vector comprises an adeno-associated viral (AAV) vector. In some embodiments, the AAV vector is AAV8. The AAV vector can be any AAV vector. In some embodiments, the invention includes a method of decreasing thymidylate synthase expression in a subject (e.g., rodent, dog, or human), the method comprising administering to the subject compositions or vectors described herein. In some embodiments, a recombinant AAV is used that includes a nucleic acid encoding the shRNA packaged in a particle comprising AAV capsid proteins. The rAAV can be of any serotype.

In some embodiments, a method of treating pancreatic cancer (e.g., PanNET) in a subject includes administering to the subject an AAV particle, a composition or vector described herein. In some embodiments, the method further comprises delivering at least one additional therapeutic agent for treatment of pancreatic cancer. In some embodiments, the at least one additional treatment comprises one or more of surgery, octreotide, doxorubicin, streptozocin, fluorouracil, capecitabine, temozolomide, cisplatin, etoposide, an mTOR inhibitor (e.g., everolimus), sunitinib, and combinations thereof.

In some embodiments, the interfering RNA is under expression control of a single promoter sequence (e.g., insulin promoter). In some embodiments, the promoter is a pancreas-specific promoter. In some embodiments, the promoter is a islet-specific promoter. In some embodiments, the islet specific promoter is an insulin promoter (e.g., a rat insulin promoter (Chai et al., Gene Therapy (2009) 16, 1202-1209; doi:10.1038/gt.2009.114; published online 3 September 2009) or a human insulin promoter (Melloul et al., Proc Natl Acad Sci USA. 1993 May 1; 90(9): 3865-3869). In some embodiments, the interfering RNA is shRNA, and wherein the shRNA is under expression control of an RNA polymerase III promoter. In some embodiments, the interfering RNA is an artificial miRNA, and wherein the artificial miRNA is under expression control of an RNA polymerase II promoter. In some embodiments, the shRNA is under expression control of a constitutive or inducible promoter.

In some embodiments, a single adeno-associated virus (AAV) vector is used to deliver the RNA agent (e.g., small hairpin RNA or artificial microRNA).

In some embodiments, small hairpin RNAs, artificial microRNAs (a-miRs) and/or RNA enzymes (ribozymes) can be designed to degrade thymidylate mRNA by targeting sequences that are common in mouse, human, and dog. Such molecules can be useful to test inhibition in cell culture, in mice, and/or in dogs, to develop inhibitors that can work in human patients.

In some embodiments, one or more of the interfering RNAs can be delivered using an adeno-associated virus (AAV) vector either as short hairpin RNAs (shRNAs) driven by a promoter (e.g., an pancreas-specific promoter, RNA polymerase III promoter or other suitable constitutive or inducible promoter) or as artificial microRNAs (miRNAs) driven by a promoter (e.g., using an RNA polymerase II promoter or other suitable constitutive or inducible promoter). In some embodiments, the pancreas-specific promoter is an islet-specific promoter. In some embodiments, the islet-specific promoter is an insulin promoter.

TABLE 1

Non-limiting sequences

| SEQ ID NO: | Name | RNA sequence |
|---|---|---|
| 1 | TSshRNA64-sense | AACCTTTGGGAGATGCACATATTTGTGAAGCCACAGATGAAATATG TGCATCTCCCAAAGTTTTTGTT |
| 2 | TS shRNA-64-antisense | AACAAAAACTTTGGGAGATGCACATATTTCATCTGTGGCTTCACAA ATATGTGCATCTCCCAAAGGTT |
| 3 | TS targeted sequence | AAAUAUGUGCAUCUCCCAAAG |
| 4 | TS targeted sequence | CUUUGGGAGAUGCACAUAUUU |
| 5 | AAV8 Capsid Sequence | Exemplary AAV8 capsid protein |

```
  1 MAADGYLPDW LEDNLSEGIR EWWALKPGAP KPKANQQKQD DGRGLVLPGY
 51 KYLGPFNGLD KGEPVNAADA AALEHDKAYD QQLQAGDNPY LRYNHADAEF
101 QERLQEDTSF GGNLGRAVFQ AKKRVLEPLG LVEEGAKTAP GKKRPVEPSP
151 QRSPDSSTGI GKKGQQPARK RLNFGQTGDS ESVPDPQPLG EPPAAPSGVG
201 PNTMAAGGGA PMADNNEGAD GVGSSSGNWH CDSTWLGDRV ITTSTRTWAL
251 PTYNNHLYKQ ISNGTSGGAT NDNTYFGYST PWGYFDFNRF HCHFSPRDWQ
301 RLINNNWGFR PKRLSFKLFN IQVKEVTQNE GTKTIANNLT STIQVFTDSE
351 YQLPYVLGSA HQGCLPPFPA DVFMIPQYGY LTLNNGSQAV GRSSFYCLEY
401 FPSQMLRTGN NFQFTYTFED VPFHSSYAHS QSLDRLMNPL IDQYLYYLSR
451 TQTTGGTANT QTLGFSQGGP NTMANQAKNW LPGPCYRQQR VSTTTGQNNN
501 SNFAWTAGTK YHLNGRNSLA NPGIAMATHK DDEERFFPSN GILIFGKQNA
551 ARDNADYSDV MLTSEEEIKT TNPVATEEYG IVADNLQQQN TAPQIGTVNS
601 QGALPGMVWQ NRDVYLQGPI WAKIPHTDGN FHPSPLMGGF GLKHPPPQIL
651 IKNTPVPADP PTTFNQSKLN SFITQYSTGQ VSVEIEWELQ KENSKRWNPE
701 IQYTSNYYKS TSVDFAVNTE GVYSEPRPIG TRYLTRNL*
```

Accordingly, compositions herein can be administered to a subject in need of treatment of pancreatic cancer. In some embodiments, the subject has or is suspected of having one or more of the conditions, diseases, and disorders disclosed herein. In some embodiments, the subject is mammal. In some embodiments, the subject is a human. In some embodiments, the subject is a non-human primate. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. Other exemplary subjects include domesticated animals such as dogs and cats; livestock such as horses, cattle, pigs, sheep, goats, and chickens; and other animals such as mice, rats, guinea pigs, and hamsters.

In some embodiments, the disclosure includes a composition comprising any recombinant adeno-associated viral (rAAV) particle or interfering RNA described herein. In some embodiments, the composition comprises one or more physiologically acceptable carriers and/or one or more physiologically acceptable adjuvants. In some embodiments, the composition comprising any recombinant adeno-associated viral (rAAV) particle or interfering RNA described herein is administered to a subject having one or more symptoms of a pancreatic condition, disease, or disorder (e.g., pancreatic cancer) or is administered after the subject has been diagnosed with a pancreatic condition, disease, or disorder (e.g., pancreatic cancer).

In some embodiments, the number of rAAV particles contained in a composition or administered to a cell or a subject may be on the order ranging from $10^6$ to $10^{14}$ particles/mL or $10^3$ to $10^{15}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are be administered. In some embodiments, the number of rAAV particles administered to a subject may be on the order ranging from $10^6$ to $10^{14}$ vector genomes (vgs)/mL or $10^3$ to $10^{15}$ vgs/mL, or any values therebetween for either range, such as for example, about $10^6$, $10^7$, $10^8$, $10^9$, $10^{10}$, $10^{11}$, $10^{12}$, $10^{13}$, or $10^{14}$ vgs/mL. In some embodiments, the number of rAAV particles administered to a subject may be on the order ranging from $10^6$ to $10^{14}$ vector genomes (vgs) or $10^3$ to $10^{15}$ vgs, or any values therebetween for either range, such as for example, about $10^3$, $10^4$, $10^5$, $10^6$, $10^7$, $10^8$, $10^9$, $10^{10}$, $10^{11}$, $10^{12}$, $10^{13}$, $10^{14}$ or $10^{15}$ vgs. In one embodiment, rAAV particles of higher than $10^{13}$ vgs/mL are administered. The rAAV particles can be administered as a single dose, or divided into two or more administrations as may be required to achieve therapy of the particular disease or disorder being treated. In some embodiments, 0.0001 mL to 10 mLs of the rAAV particles at any of the concentrations (vgs/mL) described herein are delivered to a subject.

In some embodiments, rAAV viral titers range from $1 \times 10^{10}$–$5 \times 10^{13}$ vg/ml. In some embodiments, rAAV viral titers can be $1 \times 10^{10}$, $2.5 \times 10^{10}$, $5 \times 10^{10}$, $1 \times 10^{11}$, $2.5 \times 10^{11}$, $5 \times 10^{11}$, $1 \times 10^{12}$, $2.5 \times 10^{12}$, $5 \times 10^{12}$, $1 \times 10^{13}$, $2.5 \times 10^{13}$, or $5 \times 10^{13}$ vg/mL. In some embodiments, viral titers are less than $1 \times 10^{10}$ vg/mL. In some embodiments, rAAV viral titers are greater than $1 \times 10^{15}$ vg/mL. In one embodiment, rAAV particles are greater than $5 \times 10^{13}$ vgs/mL. In some embodiments, rAAV viral titers are administered via methods further described herein.

The rAAV particles can be administered as a single dose, or divided into two or more administrations as may be required to achieve therapy of the particular disease or disorder being treated. In some embodiments, from 1 to 500 microliters of a composition described in this application is administered to a subject. For example, in some embodiments, about 1, about 10, about 50, about 100, about 200, about 300, about 400, or about 500 microliters can be administered to a subject. However, it should be appreciated that smaller or larger volumes could be administered in some embodiments.

In some embodiments, an rAAV particle, rAAV vector or interfering RNA as described herein is administered to a subject once. In some embodiments, an rAAV particle, rAAV vector or interfering RNA as described herein is administered to a subject more than once. In some embodiments, an rAAV particle, rAAV vector or interfering RNA as described herein is administered to a subject as a single dose or as multiple doses.

In some embodiments, the disclosure provides formulations of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particle or nucleic acid vectors may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, and intramuscular administration and formulation.

Typically, these formulations may contain at least about 0.1% of the therapeutic agent (e.g., rAAV particle or host cell) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver an rAAV particle or host cell in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

The pharmaceutical forms of the rAAV particle or host cell compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle or host cell is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

The compositions of the present disclosure can be delivered to the pancreas through a variety of routes. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. They can be administered prior to the onset of the condition, to prevent its occurrence, or immediately after the onset of the pathological condition or during the occurrence of an acute or protracted condition.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles or host cells in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of rAAV particle, nucleic acid vector, or host cell compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle or host cell compositions, either over a relatively short, or a relatively prolonged period of time, as may be determined by the medical practitioner overseeing the administration of such compositions.

The composition may include rAAV particles or host cells, either alone, or in combination with one or more additional active ingredients, which may be obtained from natural or recombinant sources or chemically synthesized. In some embodiments, rAAV particles are administered in combination, either in the same composition or administered as part of the same treatment regimen, with a proteasome inhibitor, such as Bortezomib, or hydroxyurea.

To "treat" a disease as the term is used herein, means to reduce the frequency or severity of at least one sign or symptom of a disease or disorder experienced by a subject, e.g., cancer such as pancreatic cancer. In some embodiments, with respect to cancer, "treat" means causing remission of the cancer, slowing the course of cancer progression, slowing or inhibiting tumor growth, and/or slowing or inhibiting tumor metastasis. In some embodiments, "treat" means slowing progression of symptoms (e.g., symptoms of pancreatic cancer) or reversing the course of the disease (e.g., the course of pancreatic cancer). The compositions described above are typically administered to a subject in an effective amount, that is, an amount capable of producing a desirable result. The desirable result will depend upon the active agent being administered. For example, an effective amount of a rAAV particle may be an amount of the particle that is capable of transferring a heterologous nucleic acid to a host organ, tissue, or cell.

Pancreatic cancers include symptoms such as pain, gastrointestinal issues, whole body fatigue or loss of appetite, dark urine, weight loss, or yellow skin and eyes. Non-functional pancreatic NET may grow for a long time without causing signs or symptoms. It may grow large or spread to other parts of the body before it causes signs or symptoms including, but not limited to, diarrhea, indigestion, a lump in the abdomen, pain in the abdomen or back, and/or yellowing of the skin and whites of the eyes.

Functional PanNETs have various signs and symptoms depending on the type of hormone being made (e.g., gastrin, insulin, glucagon, vasoactive intestinal peptide (VIP), and somatostatin). Symptoms can include stomach ulcers that keep coming back, pain in the abdomen, which may spread to the back, the pain may come and go and it may go away after taking an antacid, the flow of stomach contents back into the esophagus (gastroesophageal reflux), diarrhea, low blood sugar, this can cause blurred vision, headache, and feeling lightheaded, tired, weak, shaky, nervous, irritable, sweaty, confused, or hungry, fast heartbeat, skin rash on the face, stomach, or legs, high blood sugar, this can cause headaches, frequent urination, dry skin and mouth, or feeling hungry, thirsty, tired, or weak, blood clots, blood clots in the lung can cause shortness of breath, cough, or pain in the chest, blood clots in the arm or leg can cause pain, swelling, warmth, or redness of the arm or leg, sore tongue or sores at the corners of the mouth, very large amounts of watery diarrhea, dehydration, this can cause feeling thirsty, making less urine, dry skin and mouth, headaches, dizziness, or feeling tired, low potassium level in the blood, this can cause muscle weakness, aching, or cramps, numbness and tingling, frequent urination, fast heartbeat, and feeling confused or thirsty, cramps or pain in the abdomen, weight loss for no known reason, steatorrhea, gallstones, and/or yellowing of the skin and whites of the eyes.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Aspects of the disclosure relate to recombinant adeno-associated virus (rAAV) particles for delivery of one or more nucleic acid vectors comprising a gene of interest into various tissues, organs, and/or cells. In some embodiments, the rAAV particles comprise an rAAV capsid protein as described herein, e.g., comprising one or more amino acid substitutions. In some embodiments, the gene of interest encodes a polypeptide or protein of interest (e.g., a therapeutic polypeptide or protein). In some embodiments, the gene of interest encodes an RNA of interest (e.g., a therapeutic mRNA, siRNA, shRNA, microRNA, antisense RNA, tRNA, rRNA, or a ribozyme).

Recombinant AAV (rAAV) particles may comprise at a minimum one or more heterologous nucleic acid regions comprising a sequence encoding a gene of interest (e.g., an RNA of interest such as a siRNA or shRNA) and (b) one or more regions comprising inverted terminal repeat (ITR) sequences (e.g., wild-type ITR sequences or engineered ITR sequences) flanking the one or more heterologous nucleic acid regions. In some embodiments, the nucleic acid vector is between 4 kb and 5 kb in size (e.g., 4.2 to 4.7 kb in size). This nucleic acid vector may be encapsidated by a viral capsid, such as an AAV1, AAV2, AAV3, AAV4, AAV5, or AAV8 capsid, which may comprise a modified capsid protein as described herein. In some embodiments, the nucleic acid vector is circular. In some embodiments, the nucleic acid vector is single-stranded. In some embodiments, the nucleic acid vector is double-stranded (including partially double-stranded). In some embodiments, a double-stranded nucleic acid vector may be, for example, a self-complementary vector that contains a region of the nucleic acid vector that is complementary to another region of the nucleic acid vector, initiating the formation of the double-strandedness of the nucleic acid vector. In some embodiments, a subject is treated for pancreatic cancer with the TS shRNA described herein after diagnosis of pancreatic cancer (e.g., PanNET).

The rAAV particle may be of any AAV serotype, including any derivative or pseudotype (e.g., 1, 2, 3, 4, 5, 6, 7, 8, 9, 10, 2/1, 2/5, 2/8, or 2/9). As used herein, the serotype of an rAAV viral vector (e.g., an rAAV particle) refers to the serotype of the capsid proteins of the recombinant virus. In some embodiments, the rAAV has 1, 2, 3, 4, 5, 6, 7, 8, 9, 10, or more mutations. In some embodiments, the rAAV capsid sequence includes tyrosine to phenylalanine mutations. In some embodiments, the rAAV has 1, 2, 3 or more Y→F mutations. In some embodiments, the rAAV particle is not AAV8. In some embodiments, the rAAV particle is AAV8. In some embodiments, the rAAV particle is an AAV8 serotype comprising an rAAV capsid protein as described herein. In some embodiments, the rAAV particle is a modified AAV8. In some embodiments, the rAAV8 has 1, 2, 3 or more Y→F (tyrosine to phenylalanine) mutations. In some embodiments, the recombinant AAV8 has a Y275F, Y447F, or Y733F mutation, or any combination thereof (amino acid positions relative to the AAV8 VP1 protein, SEQ ID NO: 5)). In some embodiments, the AAV8 has both a Y447F and Y733F mutation (amino acid positions relative to the AAV8 VP1 protein, SEQ ID NO: 5).

Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan Al, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV1, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector may be combined with one or more helper plasmids, e.g., that contain a rep gene (e.g., encoding Rep78, Rep68, Rep52 and Rep40) and a cap gene (e.g., encoding VP1, VP2, and VP3, including a modified VP3 region as described herein), and transfected into a producer cell line such that the rAAV particle can be packaged and subsequently purified.

In some embodiments, the one or more helper plasmids include a first helper plasmid comprising a rep gene and a cap gene (e.g., encoding a rAAV capsid protein as described herein) and a second helper plasmid comprising a E1a gene, a E1b gene, a E4 gene, a E2a gene, and a VA gene. In some embodiments, the rep gene is a rep gene derived from AAV8 and the cap gene is derived from AAV8 and may include modifications to the gene in order to produce the modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Calif.; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise at least one of the disclosed rAAV particles or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself. In some embodiments, the host cell is a cell of erythroid lineage, such as a CD36+ burst-forming units-erythroid (BFU-E) cell or a colony-forming unit-erythroid (CFUE-E) progenitor cell.

In some embodiments, the vector is a PEMBOL-ds-INS-GFP. In some embodiments, the vector used is a vector well known in the art (e.g., Wang et al., Diabetes 2006 April; 55(4): 875-884. dx.doi.org/10.2337/diabetes.55.04.06.db05-0927; Wang et al., Gene Ther10: 2105-2111, 2003; Wang et al., Nat Biotechno123:321-328, 2005).

In some embodiments, compositions described herein (e.g., siRNA, shRNA) are formulated in a nanoparticle. In some embodiments, compositions described herein (e.g., siRNA, shRNA) are formulated in a lipid nanoparticle. In some embodiments, compositions described herein (e.g., siRNA, shRNA) are formulated in a lipid-polycation complex, referred to as a cationic lipid nanoparticle. The formation of the lipid nanoparticle may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, compositions described herein (e.g., siRNA, shRNA) are formulated in a lipid nanoparticle that includes a non-cationic lipid such as, but not limited to, cholesterol or dioleoyl phosphatidylethanolamine (DOPE).

Other Embodiments

Other Non-Limiting Embodiments of the Disclosure Include Those Below.

1. A synthetic ribonucleic acid (RNA) molecule comprising:
a sense strand of sequence AACCUUUGGGAGAUGCACAUAUUUGUGAAGCCACAGAUGAAAUAUGUGCAUCUC CCAAAGUUUUUGUU (SEQ ID NO: 1) and an antisense strand of sequence AACAAAAACUUUGGGAGAUGCACAUAUUUCAUCUGUGGCUUCACAAAUAUGUGC AUCUCCCAAAGGUU (SEQ ID NO: 2).

2. The synthetic RNA molecule of clause 1, wherein the RNA is a small hairpin RNA (shRNA).

3. A shRNA of having a targeted sequence that comprises RNA of sequence AAAUAUGUGCAUCUCCCAAAG (SEQ ID NO: 3) or RNA of sequence CUUUGGGAGAUGCACAUAUUU (SEQ ID NO: 4).

4. The synthetic RNA of any one of clauses 1 to 3, further comprising an unpaired overhang sequence at the 5' and/or 3' end.

5. The synthetic RNA of clause 4, wherein the unpaired overhang sequence comprises a sequence of repeating bases.

6. The synthetic RNA of clause 4 or 5, wherein the sequence of repeating bases comprises repeating uracil (U) bases.

7. The synthetic RNA of clause 4 or 5, wherein the unpaired overhang sequence is UU.

8. A composition comprising the synthetic RNA of any one of clauses 1 to 7.

9. The composition of clause 8, further comprising one or more physiologically acceptable carriers and/or one or more physiologically acceptable adjuvants.

10. A vector encoding the shRNA of clause 2 or 3.

11. The vector of clause 10, wherein the shRNA is selected from SEQ ID NOs: 1-4.

12. The vector of any one of clauses 9 or 10, wherein the vector is an expression plasmid.

13. The vector of any one of clauses 9-11, wherein the vector is a viral vector.

14. The viral vector of clause 12, wherein the viral vector comprises an adeno-associated viral vector.

15. A method of decreasing thymidylate synthase expression in a subject, the method comprising administering to the subject the composition of clauses 8-9 or the vector of clauses 10-14.

16. A method of treating pancreatic cancer in a subject, the method comprising administering to the subject the composition of clauses 8-9 or the vector of clauses 10-14.

17. The method of clause 16, wherein the composition or vector is delivered using an rAAV.

18. The method of clause 16, wherein the pancreatic cancer is islet cell carcinoma.

19. The method of clause 17, wherein the rAAV is AAV8.

20. The method of clause 16, wherein the interfering RNA is under expression control of promoter sequences.

21. The method of clause 20, wherein the interfering RNA is shRNA, and wherein the shRNA is under expression control of an RNA polymerase III promoter.

22. The method of clause 20, wherein the interfering RNA is shRNA, and wherein the shRNA is under expression control of a pancreas-specific promoter.

23. The method of any one of clauses 16-22, wherein the subject is a mammal.

24. The method of clause 23, wherein the mammal is a rodent or a dog.

25. The method of clause 23, wherein the mammal is a human.

26. A transgenic mouse comprising pancreatic islet cells that express human thymidylate synthase (TS) and further comprising a conditional Men1 null allele.

EXAMPLES

Example 1

Thymidylate Synthase (TS) Overexpression

It is hypothesized that human thymidylate synthase accelerates the development of MEN1-driven PanNET and that new strategies to incorporate TS inhibition within current cancer treatment will prevent development and progression of PanNET.

Thymidylate synthase, essential for cell proliferation, DNA biosynthesis and repair, exhibits oncogene-like activity. High levels of TS correlate with poor prognosis and overall survival in cancer patients. Rahman et at. (Cancer Cell. 2004 April; 5(4):341-51) describes a link between TS-regulated DNA synthesis and the induction of a neoplastic phenotype. Transgenic mice have also been shown to overexpress human TS and then subsequently develop islet hyperplasia or islet cell tumor (Chen et al. Oncogene. 2007 Jul. 19; 26(33):4817-24). Analysis of 320 gastroenteropancreatic neuroendocrine tumors identifies TS expression as independent biomarker for survival (Lee et al. Int J Cancer. 2013 Dec. 18).

The lack of suitable animal models that recapitulate human disease has limited development and testing of new treatments for PanNET. A mouse model designated hTS/Men1$^{-/-}$, where hTS is overexpressed in pancreatic islet cells carrying a conditional Men1 null allele, was established. Since hTS overexpression accelerates PanNET development in Men1 null mice the research goals focus on defining the mechanism underlying the ability of high levels of hTS to accelerate tumor growth and to develop new treatment strategies.

Elevated level of thymidylate synthase (TS) plays a direct causal role in tumorigenesis in vitro and overexpression of human TS (hTS) in transgenic mice promotes development of adenomas in the endocrine pancreas in vivo. Pancreatic islet tumor formation in hTS transgenic mice occurred with a long latency period, suggesting that additional somatic events are required to promote PanNET formation and progression. MEN1 was recently shown to be the most commonly mutated tumor suppressor gene in sporadic PanNETs (44% of PanNET patients have MEN1 mutations). Mice with conditional knockouts of Men1 gene in the pancreatic islets develop pancreatic islet tumors with long latency after homozygous inactivation of Men1 gene, suggesting that further sequential somatic events are required for tumor formation.

hTS transgenic mice were crossed with conditional Men1 null mice that normally develop pancreatic islet carcinoma with long latency. The effect of hTS overexpression on the lifespan of Men1$^{-/-}$ mice vs. hTS/Men1$^{-/-}$ mice was compared. To test whether high levels of hTS results in earlier PanNET development, hTS/Men1$^{-/-}$ and control Men1$^{-/-}$ mice were sacrificed at 5, 6.5 and 8 month of age and tumor development was compared. To determine whether hTS increase mutation frequency, hTS/Men1$^{-/-}$ mice were crossed with Big Blue® transgenic mouse that serves as a mutation detection system. Mutation frequency was analyzed in tumors isolated from hTS/Men1$^{-/-}$ and Men1$^{-/-}$ mice. AAV vectors were used (e.g., AAV8) for delivery of TS shRNA and measured TS levels, tumor progression and survival of hTS/Men1$^{-/-}$ mice.

The newly established hTS/Men1$^{-/-}$ mice model developed aggressive PanNET with 100% penetrance associated with overexpressed TS in Men1 null mice. TS expression induced islet carcinoma with shortened latency as compared to Men1$^{-/-}$ mice. The hTS/Men1$^{-/-}$ mice develop islet carcinoma as early as 6 month of age whereas Men1$^{-/-}$ mice develop islet carcinoma at 8 months of age. A significant decrease of overall survival was observed in hTS/Men1$^{-/-}$ mice as compared to Men1$^{-/-}$ mice (p<0.001). In addition, it was observed that overexpression of TS results in the increase of mutational frequency in tumors derived from the hTS/Men1$^{-/-}$ as compared to control Men1$^{-/-}$ mice. Mutations such as transitions, transversions, insertions and deletions were 3.2 fold higher in tumors isolated from hTS/Men1$^{-/-}$ as compared to control Men1$^{-/-}$ mice. It was shown that high levels of TS increase mutational frequency that may accelerate PanNET progression in hTS/Men1$^{-/-}$ mice. To evaluate the effect of TS inhibition in PanNET progression, AAV-TS shRNA was delivered to the endocrine pancreas of hTS/Men1$^{-/-}$ mice and it was shown that AAV-TS shRNA, specifically targeted pancreatic islet cells, decreased TS expression, significantly decreased PanNET progression and increased survival of hTS/Men1$^{-/-}$ mice.

The conversion of deoxyuridine monophosphate (dUMP) to deoxythymidine monophosphate (dTMP) with thymidylate synthetase is shown in FIG. 1.

Figure 2A:
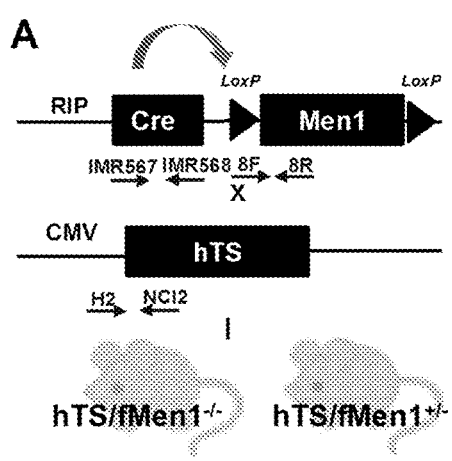
FIGS. 2A-2D show generation of novel hTS/Men1$^{-/-}$ genetically engineered mouse model.
Figure 2B:
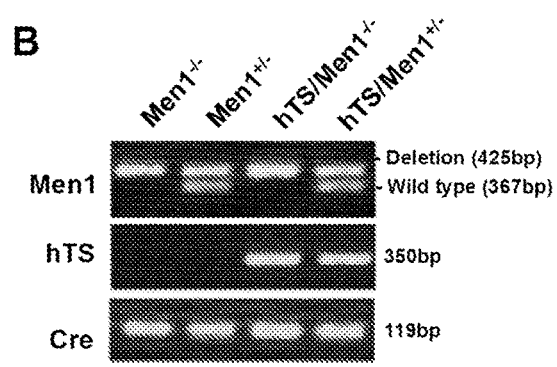
Figure 2C:
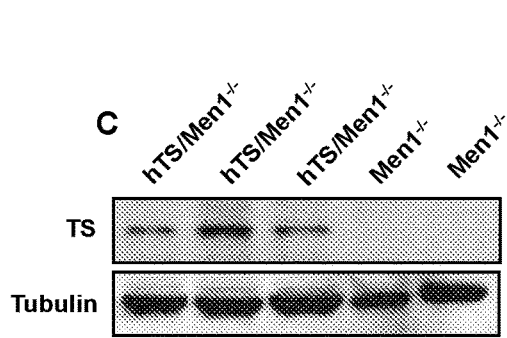
Figure 2D:
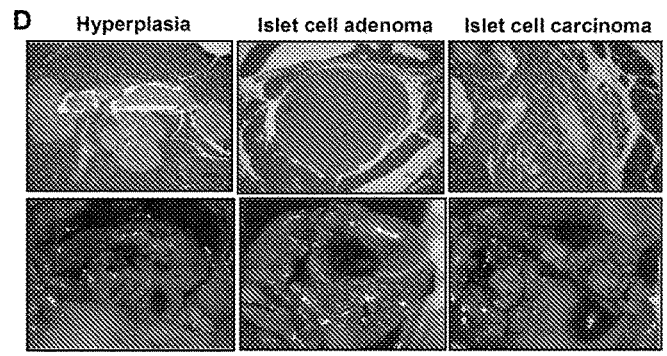

FIGS. 2A-2D show generation of novel hTS/Men1$^{-/-}$ genetically engineered mouse model. FIG. 2A shows schematic representation of breeding strategy. Arrows indicate primer location for genotyping analysis. FIG. 2B shows genotyping results of hTS/Men1$^{-/-}$ and Men1$^{-/-}$ mice. FIG. 2C shows immunoblot anlaysis for TS expression in the pancreases of hTS/Men1$^{-/-}$ and Men1$^{-/-}$ mice. FIG. 2D shows PanNET progression of hTS/Men1$^{-/-}$ GEMMs. Representative H&E images and pathological photographs of pancreatic islet lesions in hTS/fMen1$^{-/-}$ mice (Scale bar, 100 μm).

Figure 3D:
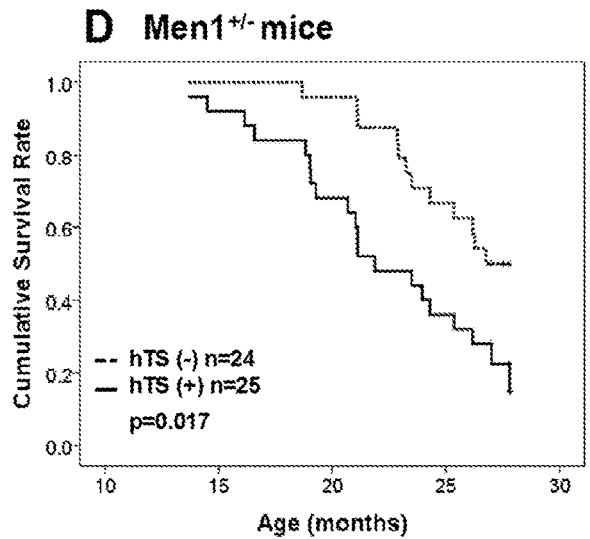
Figure 3E:
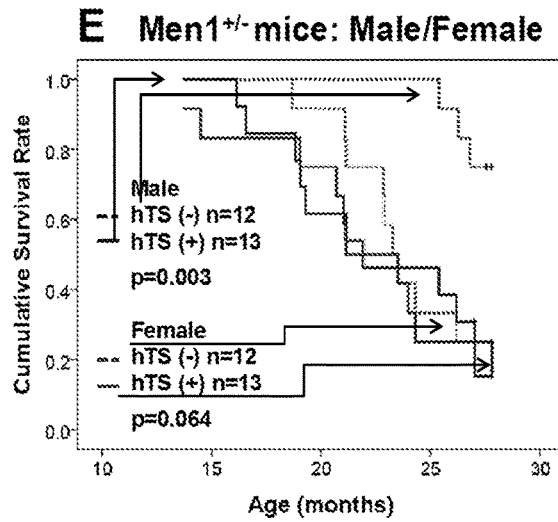

FIGS. 3A-3E show hTS overexpression significantly reduced survival of Men1-null mice. FIG. 3A shows overall survival analysis of total Men1$^{-/-}$ vs. hTS/Men1$^{-/-}$ mice. FIG. 3B shows survival analysis of Men1$^{-/-}$ vs. hTS/Men1$^{-/-}$ mice that developed only PanNETs. (FIG. 3C) mice. FIG. 3D shows overall survival analysis of total Men1$^{+/-}$ vs. hTS/Men1$^{+/-}$ mice. FIG. 3E shows separate survival analysis of male and female.

Figure 4A:
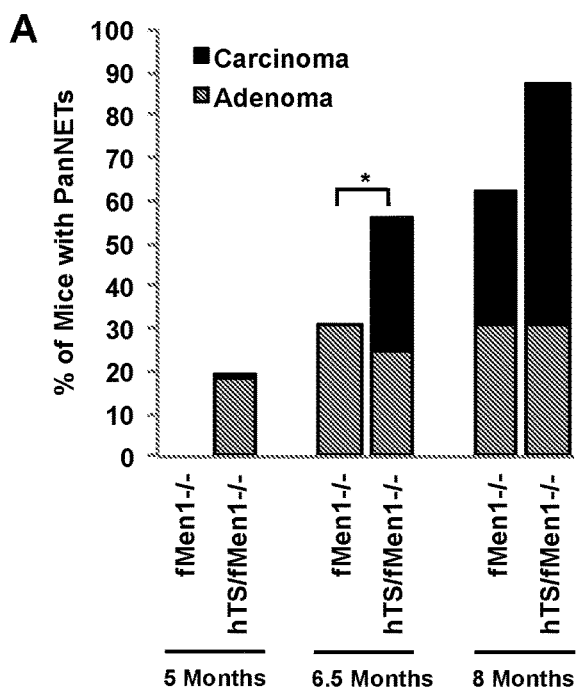
FIGS. 4A-4B show TS overexpression induces PanNET progression.
Figure 4B:
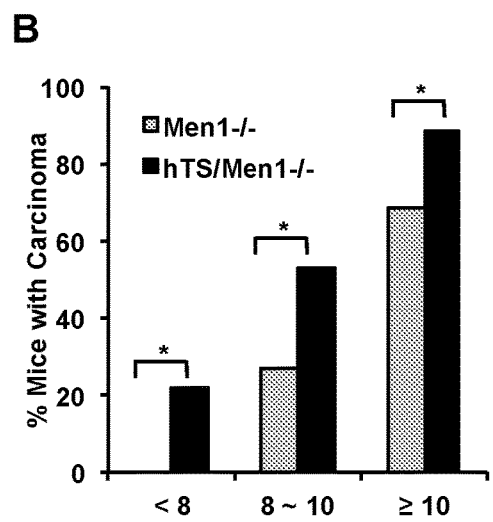

FIGS. 4A-4B show TS overexpression induces PanNET progression. FIG. 4A shows Pancreatic islet lesions in Men1$^{-/-}$ vs. hTS/Men1$^{-/-}$ mice. Animals were euthanized at 5, 6.5 and 8 months and pancreas were isolated for histopathologic analysis (n=16 per group at each time point). FIG. 4B shows pancreatic islet carcinoma incidence. The percentage of mice with islet tumor lesions is shown (*p<0.01, **p<0.001).

FIGS. 5A-5C show TS overexpression induces somatic mutations. FIG. 5A shows an overview of the λ Select-cII Mutation Detection System. FIG. 5B shows mutation frequencies in Men1$^{-/-}$/BB and hTS/fMen1$^{-/-}$/BB mice (n=3 per group at each time point). FIG. 5C shows the type of mutations in the pancreas and tumors of Men1$^{-/-}$/BB and hTS/Men1$^{-/-}$/BB mice at 5 and 10 months of age.

Figure 6A:
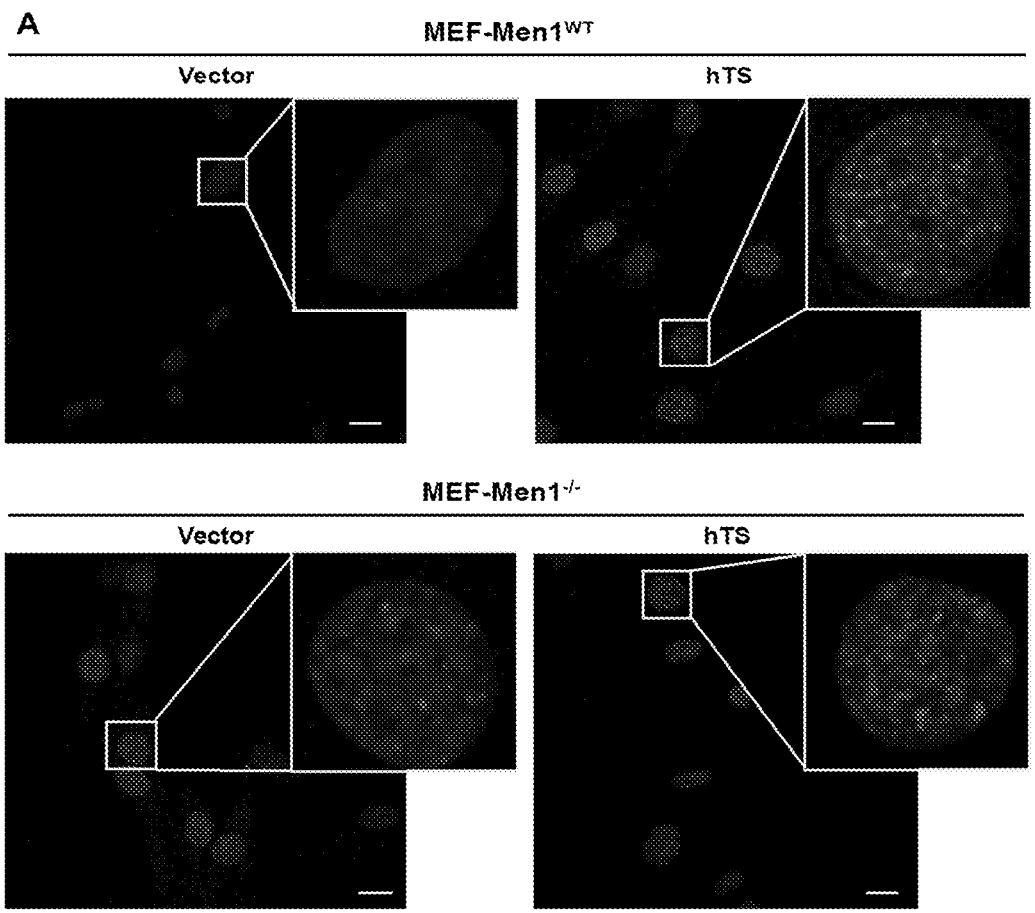
FIGS. 6A-6B show overexpression induces DNA double strand breaks.
Figure 6B:
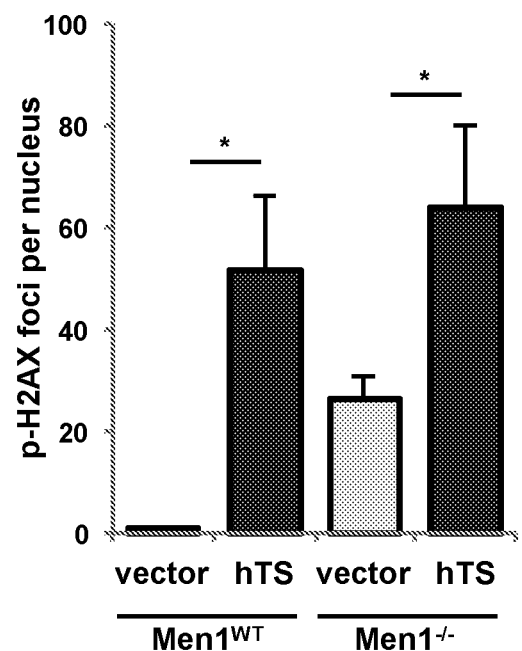

FIGS. 6A-6B show overexpression induces DNA double strand breaks. FIG. 6A shows an immunofluorescence image of λH2AX foci in MEF-Men1$^{WT}$-vector, MEF-Men1$^{WT}$-hTS cells, MEF Men1$^{-/-}$-vector and MEF-Men1$^{-/-}$-hTS cells. Representative nuclei are shown (Scale bars, 10 μm). FIG. 6B shows quantification of γH2AX foci (*p<0.01).

Figure 7A:
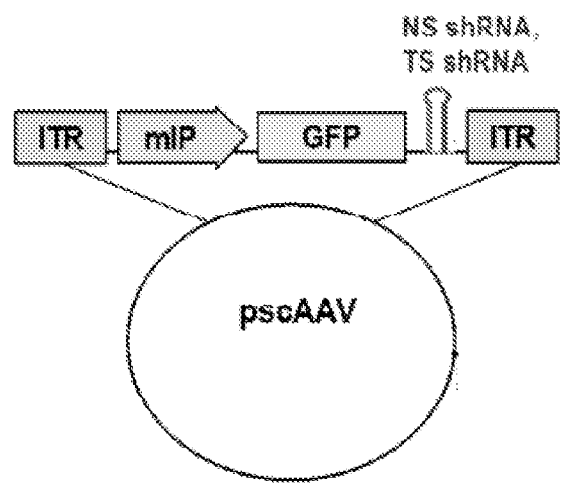
FIGS. 7A-7F show AAV-TS shRNA inhibits PanNET progression.
Figure 7B:
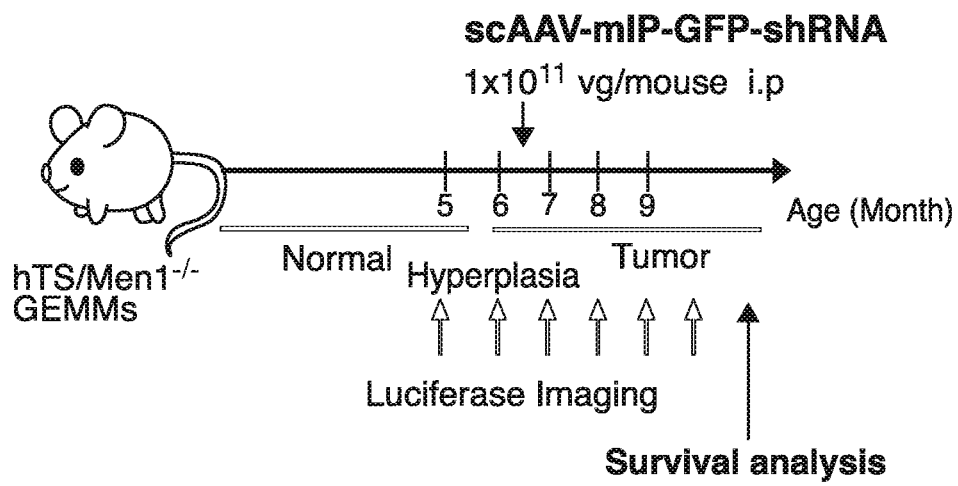
Figure 7C:
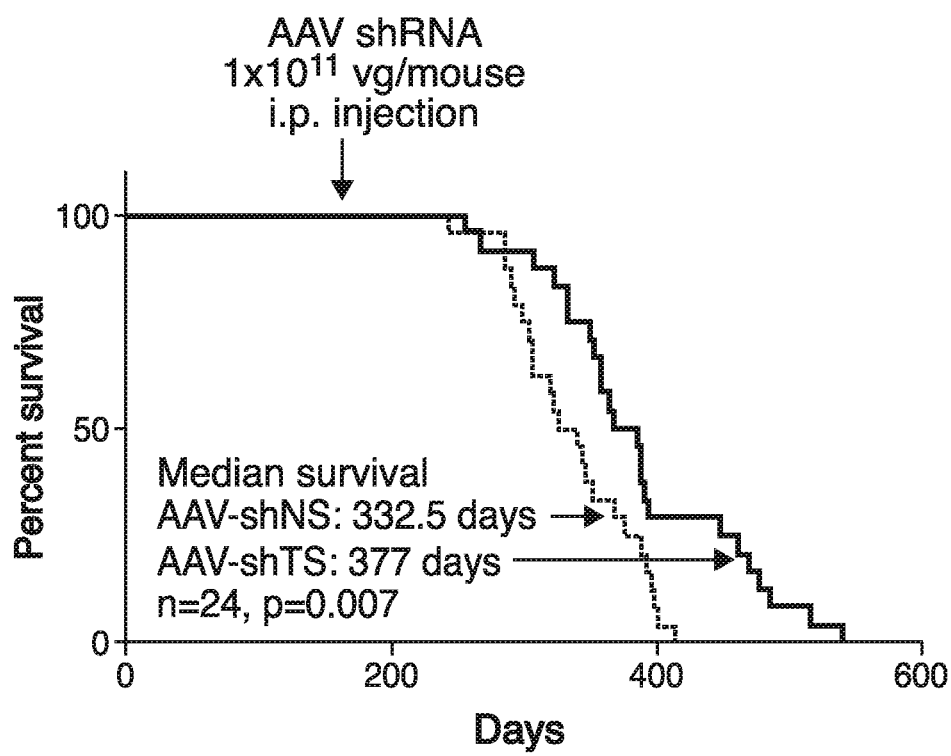
Figure 7D:
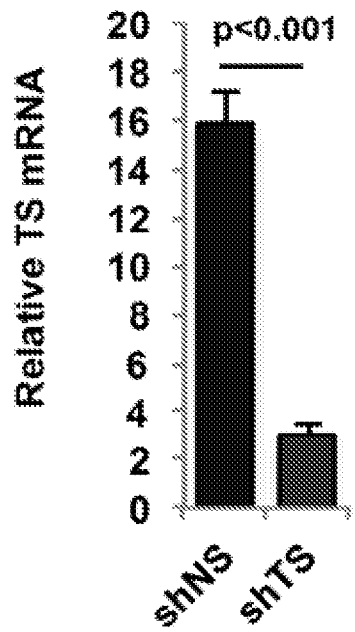
Figure 7E:
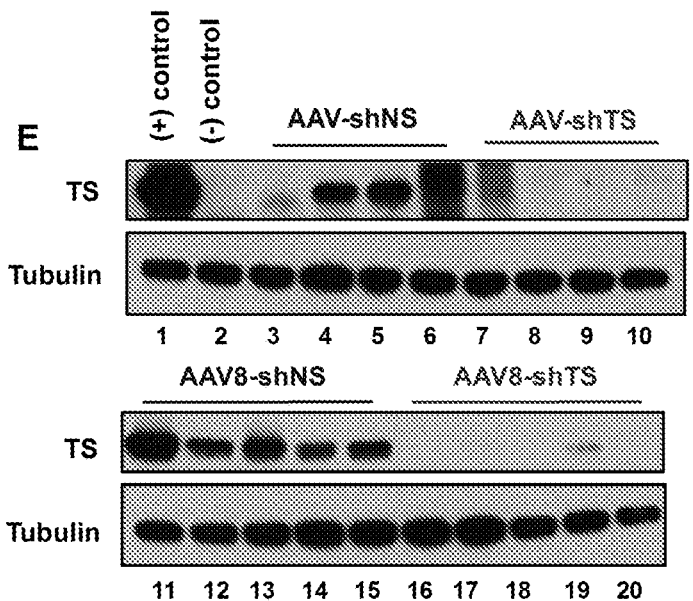
Figure 7F:
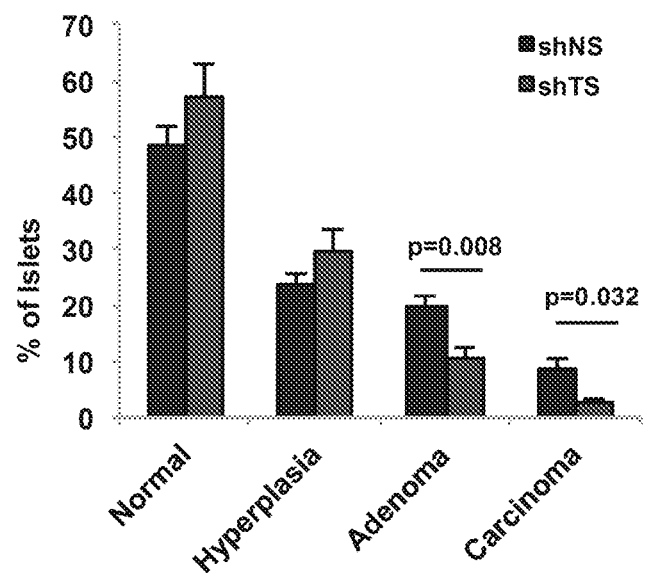

FIGS. 7A-7F show AAV-TS shRNA inhibits PanNET progression. FIG. 7A shows a vector map of scAAV-mIP-GFP-NSshRNA and scAAV-mIP-GFP-TSshRNA (containing SEQ ID NO:1 and 2) construct. FIG. 7B shows schematics of scAAV-mIP-GFP-NSshRNA (AAV-shNS) or scAAV-mIP-GFP-TSshRNA (AAV-shTS) treatment in hTS/Men1$^{-/-}$ mice. FIG. 7C shows survival analysis of pancreas tissues from hTS/Men1 mice after TS shRNA injection (n=24 per group). FIG. 7D shows TS mRNA expression levels in tumors. FIG. 7E shows TS protein expression levels in tumors. FIG. 7F shows the percentage of islet tumor lesion (n=9 per group).

The novel animal model described herein will allow development of new strategies for targeting TS in combination with other FDA approved drugs for the treatment of PanNET. The data provided herein also show that an interfering RNA (e.g., shRNA) that targets TS can be delivered using AAV and is effective for treating pancreatic cancer.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A recombinant adeno-associated viral (rAAV) particle comprising a nucleic acid vector that comprises (a) a heterologous nucleic acid region comprising a sequence that encodes an interfering RNA that comprises a region of complementarity with a thymidylate synthase mRNA, wherein the interfering RNA comprises the sequence of any of SEQ ID NOs: 1 or 2, and (b) inverted terminal repeat (ITR) sequences flanking the heterologous nucleic acid region.

2. The rAAV particle of claim 1, wherein the interfering RNA is a small hairpin RNA (shRNA) or a microRNA.

3. The rAAV particle of claim 1, wherein the region of complementarity is 100% complementary to at least 8 contiguous nucleotides of any of SEQ ID NOs: 6-11.

4. The rAAV particle of claim 1, wherein the particle is an AAV8 particle or a modified AAV8 particle, wherein the modified AAV8 particle comprises an AAV8 capsid protein comprising a Y275F, Y447F, or Y733F mutation, or any combination thereof, relative to the AAV8 VP1 amino acid sequence set forth in SEQ ID NO: 5.

5. The rAAV particle of claim 4, wherein the AAV8 capsid protein comprises Y447F and Y733F mutations.

6. The rAAV particle of claim 1, wherein the interfering RNA is under expression control of a promoter.

7. The rAAV particle of claim 6, wherein the interfering RNA is under expression control of an RNA polymerase III promoter.

8. The rAAV particle of claim 6, wherein the interfering RNA is under expression control of a pancreas-specific promoter, optionally wherein the pancreas-specific promoter is an islet-specific promoter, further optionally wherein the islet-specific promoter is an insulin promoter.

9. A composition comprising the rAAV particle of claim 1.

10. A synthetic ribonucleic acid (RNA) molecule comprising:
a sense strand of sequence AACCUUUGGGAGAUGCACAUAUUUGUGAAGCCACAGAUGAAAUAUGUGCAUCUCCC AAAGUUUUUGUU (SEQ ID NO: 1) and an antisense strand of sequence AACAAAAACUUUGGGAGAUGCACAUAUUUCAUCUGUGGCUUCACAAAUAUGUGCAU CUCCCAAAGGUU (SEQ ID NO: 2).

11. The synthetic RNA molecule of claim 10, wherein the RNA is a small hairpin RNA (shRNA).

12. A composition comprising the synthetic RNA of claim 10.

13. The composition of claim 12, further comprising one or more physiologically acceptable carriers and/or one or more physiologically acceptable adjuvants.

14. A host cell comprising the rAAV particle of claim 1.

15. A host cell comprising a nucleic acid vector that comprises a heterologous nucleic acid region comprising a sequence that encodes an interfering RNA that comprises a region of complementarity with a thymidylate synthase mRNA, wherein the interfering RNA comprises the sequence of any of SEQ ID NOs: 1 or 2.

* * * * *

SEQUENCE LISTING

```
<160> NUMBER OF SEQ ID NOS: 11

<210> SEQ ID NO 1
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 1
```

```
aaccuuuggg agaugcacau auuugugaag ccacagauga aauaugugca ucucccaaag    60
uuuuuguu                                                              68
```

<210> SEQ ID NO 2
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 2

```
aacaaaaacu ugggagaug cacauauuuc aucuguggcu ucacaaauau gugcaucucc    60
caaagguu                                                              68
```

<210> SEQ ID NO 3
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 3

```
aaauaugugc aucucccaaa g                                               21
```

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4

```
cuuugggaga ugcacauauu u                                               21
```

<210> SEQ ID NO 5
<211> LENGTH: 738
<212> TYPE: PRT
<213> ORGANISM: Adeno-associated virus 8

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

```
Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
            530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
            565                 570                 575
```

```
Glu Glu Tyr Gly Ile Val Ala Asp Asn Leu Gln Gln Asn Thr Ala
            580                 585                 590
Pro Gln Ile Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
            660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
    690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 6
<211> LENGTH: 1524
<212> TYPE: DNA
<213> ORGANISM: Artificial Sequence
<220> FEATURE:
<223> OTHER INFORMATION: Synthetic Polynucleotide

<400> SEQUENCE: 6
cgcgccactt ggcctgcctc cgtcccgccg cgccacttcg cctgcctccg tccccgccc      60
gccgcgccat gcctgtggcc ggctcggagc tgccgcgccg cccttgccc ccgccgcac     120
aggagcggga cgccgagccg cgtccgccgc acggggagct gcagtacctg ggcagatcc     180
aacacatcct ccgctgcggc gtcaggaagg acgaccgcac gggcaccggc accctgtcgg   240
tattcggcat gcaggcgcgc tacagcctga gagatgaatt ccctctgctg acaaccaaac   300
gtgtgttctg gaagggtgtt ttggaggagt tgctgtggtt tatcaaggga tccacaaatg   360
ctaaagagct gtcttccaag ggagtgaaaa tctgggatgc caatggatcc cgagactttt   420
tggacagcct gggattctcc accagagaag aaggggactt gggcccagtt tatggcttcc   480
agtggaggca ttttggggca gaatacagag atatggaatc agattattca ggacagggag   540
ttgaccaact gcaaagagtg attgacacca tcaaaaccaa ccctgacgac agaagaatca   600
tcatgtgcgc ttggaatcca agagatcttc ctctgatggc gctgcctcca tgccatgccc   660
tctgccagtt ctatgtggtg aacagtgagc tgtcctgcca gctgtaccag agatcgggag   720
acatgggcct cggtgtgcct ttcaacatcg ccagctacgc cctgctcacg tacatgattg   780
cgcacatcac gggcctgaag ccaggtgact ttatacacac tttgggagat gcacatattt   840
acctgaatca catcgagcca ctgaaaattc agcttcagcg agaacccaga cctttcccaa   900
agctcaggat tcttcgaaaa gttgagaaaa ttgatgactt caaagctgaa gactttcaga   960
ttgaagggta caatccgcat ccaactatta aatggaaat ggctgtttag ggtgctttca    1020
aaggagcttg aaggatattg tcagtcttta ggggttgggc tggatgccga ggtaaaagtt   1080
ctttttgctc taaagaaga aggaactagg tcaaaaatct gtccgtgacc tatcagttat    1140
```

| | | |
|---|---|---|
| taatttttaa ggatgttgcc actggcaaat gtaactgtgc cagttctttc cataataaaa | 1200 | |
| ggctttgagt taactcactg agggtatctg acaatgctga ggttatgaac aaagtgagga | 1260 | |
| gaatgaaatg tatgtgctct tagcaaaaac atgtatgtgc atttcaatcc cacgtactta | 1320 | |
| taaagaaggt tggtgaattt cacaagctat ttttggaata tttttagaat attttaagaa | 1380 | |
| tttcacaagc tattccctca aatctgaggg agctgagtaa caccatcgat catgatgtag | 1440 | |
| agtgtggtta tgaactttat agttgtttta tatgttgcta taataagaa gtgttctgca | 1500 | |
| ttcgtaaaaa aaaaaaaaaa aaaa | 1524 | |

<210> SEQ ID NO 7
<211> LENGTH: 1569
<212> TYPE: DNA
<213> ORGANISM: Artificial Sequence
<220> FEATURE:
<223> OTHER INFORMATION: Synthetic Polynucleotide

<400> SEQUENCE: 7

| | | |
|---|---|---|
| gggggcgcgc ggaagggtc ctgccaccgc gccacttggc ctgcctccgt cccgccgcgc | 60 | |
| cacttcgcct gcctccgtcc cccgcccgcc gcgccatgcc tgtggccggc tcggagctgc | 120 | |
| cgcgccggcc cttgccccc gccgcacagg agcgggacgc cgagccgcgt ccgccgcacg | 180 | |
| gggagctgca gtacctgggg cagatccaac acatcctccg ctgcggcgtc aggaaggacg | 240 | |
| accgcacggg caccggcacc ctgtcggtat tcggcatgca ggcgcgctac agcctgagag | 300 | |
| atgaattccc tctgctgaca accaaacgtg tgttctggaa gggtgttttg gaggagttgc | 360 | |
| tgtggtttat caagggatcc acaaatgcta aagagctgtc ttccaaggga gtgaaaatct | 420 | |
| gggatgccaa tggatcccga gactttttgg acagcctggg attctccacc agagaagaag | 480 | |
| gggacttggg cccagtttat ggcttccagt ggaggcattt tggggcagaa tacagagata | 540 | |
| tggaatcaga ttattcagga cagggagttg accaactgca aagagtgatt gacaccatca | 600 | |
| aaaccaaccc tgacgacaga agaatcatca tgtgcgcttg gaatccaaga gatcttcctc | 660 | |
| tgatggcgct gcctccatgc catgccctct gccagttcta tgtggtgaac agtgagctgt | 720 | |
| cctgccagct gtaccagaga tcgggagaca tgggcctcgg tgtgccttc aacatcgcca | 780 | |
| gctacgccct gctcacgtac atgattgcgc acatcacggg cctgaagcca ggtgacttta | 840 | |
| tacacacttt gggagatgca catatttacc tgaatcacat cgagccactg aaaattcagc | 900 | |
| ttcagcgaga acccagacct ttcccaaagc tcaggattct tcgaaagtt gagaaaattg | 960 | |
| atgacttcaa agctgaagac tttcagattg aagggtacaa tccgcatcca actattaaaa | 1020 | |
| tggaaatggc tgtttagggt gctttcaaag gagctcgaag gatattgtca gtctttaggg | 1080 | |
| gttgggctga tgccgaggt aaagttctt tttgctctaa aagaaaagg aactaggtca | 1140 | |
| aaaatctgtc cgtgacctat cagttattaa ttttttaagga tgttgccact ggcaaatgta | 1200 | |
| actgtgccag ttcttccat aataaaaggc tttgagttaa ctcactgagg gtatctgaca | 1260 | |
| atgctgaggt tatgaacaaa gtgaggagaa tgaaatgtat gtgctcttag caaaaacatg | 1320 | |
| tatgtgcatt tcaatcccac gtacttataa agaaggttgg tgaatttcac aagctatttt | 1380 | |
| tggaatattt tagaatatt ttaagaattt cacaagctat tccctcaaat ctgagggagc | 1440 | |
| tgagtaacac catcgatcat gatgtagagt gtggttatga actttaaagt tatagttgtt | 1500 | |
| ttatatgttg ctataataaa gaagtgttct gcattcgcca aaaaaaaaaa aaaaaaaaa | 1560 | |
| aaaaaaaaa | 1569 | |

<210> SEQ ID NO 8
<211> LENGTH: 942
<212> TYPE: DNA
<213> ORGANISM: Artificial Sequence
<220> FEATURE:
<223> OTHER INFORMATION: Synthetic Polynucleotide

<400> SEQUENCE: 8

| | | | | | |
|---|---|---|---|---|---|
| atgcctgtgg | ccggctcgga | gctgccgcgc | cggcccttgc | ccccgccgc | 60 |
| gacgccgagc | cgcgtccgcc | gcacggggag | ctgcagtacc | tggggcagat | ccaacacatc | 120 |
| ctccgctgcg | cgtcaggaa | ggacgaccgc | acgggcaccg | gcaccctgtc | ggtattcggc | 180 |
| atgcaggcgc | gctacagcct | gagagatgaa | ttccctctgc | tgacaaccaa | acgtgtgttc | 240 |
| tggaagggtg | ttttggagga | gttgctgtgg | tttatcaagg | gatccacaaa | tgctaaagag | 300 |
| ctgtcttcca | agggagtgaa | aatctgggat | gccaatggat | cccgagactt | tttggacagc | 360 |
| ctgggattct | ccaccagaga | agaagggac | ttgggcccag | tttatggctt | ccagtggagg | 420 |
| cattttgggg | cagaatacag | agatatggaa | tcagattatt | caggacaggg | agttgaccaa | 480 |
| ctgcaaagag | tgattgacac | catcaaaacc | aaccctgacg | acagaagaat | catcatgtgc | 540 |
| gcttggaatc | caagagatct | tcctctgatg | gcgctgcctc | catgccatgc | cctctgccag | 600 |
| ttctatgtgg | tgaacagtga | gctgtcctgc | cagctgtacc | agagatcggg | agacatgggc | 660 |
| ctcggtgtgc | ctttcaacat | cgccagctac | gccctgctca | cgtacatgat | tgcgcacatc | 720 |
| acgggcctga | agccaggtga | ctttatacac | actttgggag | atgcacatat | ttacctgaat | 780 |
| cacatcgagc | cactgaaaat | tcagcttcag | cgagaaccca | gaccttttccc | aaagctcagg | 840 |
| attcttcgaa | aagttgagaa | aattgatgac | ttcaaagctg | aagactttca | gattgaaggg | 900 |
| tacaatccgc | atccaactat | taaaatggaa | atggctgttt | tg | 942 |

<210> SEQ ID NO 9
<211> LENGTH: 942
<212> TYPE: DNA
<213> ORGANISM: Artificial Sequence
<220> FEATURE:
<223> OTHER INFORMATION: Synthetic Polynucleotide

<400> SEQUENCE: 9

| | | | | | |
|---|---|---|---|---|---|
| atgcctgtgg | ccggctcgga | gctgccgcgc | cggcccttgc | ccccgccgc | 60 |
| gacgccgagc | cgcgtccgcc | gcacggggag | ctgcagtacc | tggggcagat | ccaacacatc | 120 |
| ctccgctgcg | cgtcaggaa | ggacgaccgc | acgggcaccg | gcaccctgtc | ggtattcggc | 180 |
| atgcaggcgc | gctacagcct | gagagatgaa | ttccctctgc | tgacaaccaa | acgtgtgttc | 240 |
| tggaagggtg | ttttggagga | gttgctgtgg | tttatcaagg | gatccacaaa | tgctaaagag | 300 |
| ctgtcttcca | agggagtgaa | aatctgggat | gccaatggat | cccgagactt | tttggacagc | 360 |
| ctgggattct | ccaccagaga | agaagggac | ttgggcccag | tttatggctt | ccagtggagg | 420 |
| cattttgggg | cagaatacag | agatatggaa | tcagattatt | caggacaggg | agttgaccaa | 480 |
| ctgcaaagag | tgattgacac | catcaaaacc | aaccctgacg | acagaagaat | catcatgtgc | 540 |
| gcttggaatc | caagagatct | tcctctgatg | gcgctgcctc | catgccatgc | cctctgccag | 600 |
| ttctatgtgg | tgaacagtga | gctgtcctgc | cagctgtacc | agagatcggg | agacatgggc | 660 |
| ctcggtgtgc | ctttcaacat | cgccagctac | gccctgctca | cgtacatgat | tgcgcacatc | 720 |
| acgggcctga | agccaggtga | ctttatacac | actttgggag | atgcacatat | ttacctgaat | 780 |
| cacatcgagc | cactgaaaat | tcagcttcag | cgagaaccca | gaccttttccc | aaagctcagg | 840 |

```
attcttcgaa aagttgagaa aattgatgac ttcaaagctg aagactttca gattgaaggg    900
tacaatccgc atccaactat taaaatggaa atggctgttt ag                       942
```

<210> SEQ ID NO 10
<211> LENGTH: 942
<212> TYPE: DNA
<213> ORGANISM: Artificial Sequence
<220> FEATURE:
<223> OTHER INFORMATION: Synthetic Polynucleotide

<400> SEQUENCE: 10

```
atgcctgtgg ccggctcgga gctgccgcgc cggcccttgc ccccgccgc acaggagcgg     60 gacgccgagc cgcgtccgcc gcacggggag ctgcagtacc tggggcagat ccaacacatc   120
ctccgctgcg cgtcaggaa ggacgaccgc acgggcaccg gcaccctgtc ggtattcggc    180
atgcaggcgc gctacagcct gagagatgaa ttccctctgc tgacaaccaa acgtgtgttc   240
tggaagggtg ttttggagga gttgctgtgg tttatcaagg gatccacaaa tgctaaagag   300
ctgtcttcca agggagtgaa aatctgggat gccaatggat cccgagactt tttggacagc   360
ctgggattct ccaccagaga agaagggac ttgggcccag tttatggctt ccagtggagg    420 catttgggg cagaatacag agatatggaa tcagattatt caggacaggg agttgaccaa   480
ctgcaaagag tgattgacac catcaaaacc aaccctgacg acagaagaat catcatgtgc   540
gcttggaatc caagagatct tcctctgatg gcgctgcctc catgccatgc cctctgccag   600
ttctatgtgg tgaacagtga gctgtcctgc agctgtacc agagatcggg agacatgggc   660
ctcggtgtgc ctttcaacat cgccagctac gccctgctca cgtacatgat tgcgcacatc   720
acgggcctga gccaggtga ctttatacac actttgggag atgcacatat ttacctgaat   780
cacatcgagc cactgaaaat tcagcttcag cgagaaccca gacctttccc aaagctcagg   840
attcttcgaa aagttgagaa aattgatgac ttcaaagctg aagactttca gattgaaggg   900
tacaatccgc atccaactat taaaatggaa atggctgttt tg                       942
```

<210> SEQ ID NO 11
<211> LENGTH: 942
<212> TYPE: DNA
<213> ORGANISM: Artificial Sequence
<220> FEATURE:
<223> OTHER INFORMATION: Synthetic Polynucleotide

<400> SEQUENCE: 11

```
atgcctgtgg ccggctcgga gctgccgcgc cggcccttgc ccccgccgc acaggagcgg     60 gacgccgagc cgcgtccgcc gcacggggag ctgcagtacc tggggcagat ccaacacatc   120
ctccgctgcg cgtcaggaa ggacgaccgc acgggcaccg gcaccctgtc ggtattcggc    180
atgcaggcgc gctacagcct gagagatgaa ttccctctgc tgacaaccaa acgtgtgttc   240
tggaagggtg ttttggagga gttgctgtgg tttatcaagg gatccacaaa tgctaaagag   300
ctgtcttcca agggagtgaa aatctgggat gccaatggat cccgagactt tttggacagc   360
ctgggattct ccaccagaga agaagggac ttgggcccag tttatggctt ccagtggagg    420 catttgggg cagaatacag agatatggaa tcagattatt caggacaggg agttgaccaa   480
ctgcaaagag tgattgacac catcaaaacc aaccctgacg acagaagaat catcatgtgc   540
gcttggaatc caagagatct tcctctgatg gcgctgcctc catgccatgc cctctgccag   600
ttctatgtgg tgaacagtga gctgtcctgc agctgtacc agagatcggg agacatgggc   660
```

```
ctcggtgtgc ctttcaacat cgccagctac gccctgctca cgtacatgat tgcgcacatc    720
acgggcctga agccaggtga ctttatacac actttgggag atgcacatat ttacctgaat    780
cacatcgagc cactgaaaat tcagcttcag cgagaaccca gacctttccc aaagctcagg    840
attcttcgaa aagttgagaa aattgatgac ttcaaagctg aagactttca gattgaaggg    900
tacaatccgc atccaactat taaaatggaa atggctgttt ag                       942
```